United States Patent
Ogiwara et al.

(10) Patent No.: US 8,643,268 B2
(45) Date of Patent: Feb. 4, 2014

(54) ORGANIC ELECTROLUMINESCENCE DEVICE

(75) Inventors: Toshinari Ogiwara, Sodegaura (JP); Chishio Hosokawa, Sodegaura (JP)

(73) Assignee: Idemitsu Kosan Co., Ltd., Tokyo (JP)

(*) Notice: Subject to any disclaimer, the term of this patent is extended or adjusted under 35 U.S.C. 154(b) by 0 days.

(21) Appl. No.: 13/428,314

(22) Filed: Mar. 23, 2012

(65) Prior Publication Data

US 2012/0248968 A1 Oct. 4, 2012

Related U.S. Application Data

(60) Provisional application No. 61/467,703, filed on Mar. 25, 2011.

(30) Foreign Application Priority Data

Mar. 25, 2011 (JP) .................................. 2011-068758

(51) Int. Cl.
*H01L 51/54* (2006.01)

(52) U.S. Cl.
USPC .......................................... 313/504; 428/690

(58) Field of Classification Search
USPC .................................. 313/498–512
See application file for complete search history.

(56) References Cited

U.S. PATENT DOCUMENTS

| | | |
|---|---|---|
| 2003/0205696 A1* | 11/2003 | Thoms et al. ............. 252/301.16 |
| 2004/0086745 A1 | 5/2004 | Iwakuma et al. |
| 2005/0158578 A1 | 7/2005 | Iwakuma et al. |
| 2005/0249976 A1 | 11/2005 | Iwakuma et al. |
| 2006/0051616 A1 | 3/2006 | Suzuki et al. |
| 2009/0001882 A1* | 1/2009 | Park et al. ..................... 313/504 |
| 2009/0179552 A1* | 7/2009 | Froehlich et al. ............. 313/504 |
| 2010/0090209 A1 | 4/2010 | Ikari et al. |
| 2010/0090238 A1 | 4/2010 | Mori et al. |
| 2010/0090592 A1 | 4/2010 | Shiobara et al. |
| 2010/0090593 A1 | 4/2010 | Mori et al. |
| 2010/0141129 A1* | 6/2010 | Fukuoka et al. ............. 313/504 |

(Continued)

FOREIGN PATENT DOCUMENTS

| | | |
|---|---|---|
| JP | 2004-241374 | 8/2004 |
| JP | 2006-024830 | 1/2006 |

(Continued)

OTHER PUBLICATIONS

Endo, Ayataka et al., "Efficient Up-Conversion of Triplet Excitons into a Singlet State and Its Application for Organic Light Emitting Diodes," Applied Physics Letters, 2011, vol. 98, pp. 083302-1-083302-3.

(Continued)

*Primary Examiner* — Donald Raleigh
(74) *Attorney, Agent, or Firm* — Ditthavong Mori & Steiner, P.C.

(57) ABSTRACT

An organic EL device includes a pair of electrodes and an organic compound layer between pair of electrodes. The organic compound layer includes an emitting layer including a first material and a second material. The second material is a fluorescent material. Singlet energy EgS(H) of the first material and singlet energy EgS(D) of the second material satisfy a relationship of the following formula (1). The first material satisfies a relationship of the following formula (2) in terms of a difference $\Delta ST(H)$ between the singlet energy EgS(H) and an energy gap $Eg_{77K}(H)$ at 77K.

$$EgS(H) > EgS(D) \qquad (1)$$

$$\Delta ST(H) = EgS(H) - Eg_{77K}(H) < 0.3 \text{ (eV)} \qquad (2)$$

6 Claims, 10 Drawing Sheets

(56) References Cited

U.S. PATENT DOCUMENTS

| | | |
|---|---|---|
| 2010/0171417 A1 | 7/2010 | Kitamura et al. |
| 2010/0187977 A1 | 7/2010 | Kai et al. |
| 2011/0278555 A1 | 11/2011 | Inoue et al. |
| 2011/0279020 A1 | 11/2011 | Inoue et al. |
| 2012/0138911 A1 | 6/2012 | Inoue et al. |
| 2012/0138912 A1 | 6/2012 | Inoue et al. |

FOREIGN PATENT DOCUMENTS

| | | |
|---|---|---|
| WO | WO-03/080760 A1 | 10/2003 |
| WO | WO-03/080761 A1 | 10/2003 |
| WO | WO-2004/092111 A1 | 10/2004 |
| WO | WO-2010/134350 A1 | 11/2010 |
| WO | WO-2010/134352 A1 | 11/2010 |
| WO | WO-2011/070963 A1 | 6/2011 |
| WO | WO-2011/132683 A1 | 10/2011 |

OTHER PUBLICATIONS

Adachi, C. "Expression of Thermally-Activated Delayed Fluorescence of High Efficiency and Application Thereof to Oled", Organic El Symposium, proceeding for the tenth meeting held on Jun. 17 (Thurs.) to 18 (Fri.) in 2010, pp. 11-12.

Das, S. et al. "Can H-Aggregates Serve as Light-Harvesting Antennae? Triplet-Triplet Energy Transfer between Excited Aggregates and Monomer Thionine in Aersol-OT Solutions", J. Phys. Chem. B, 1999, vol. 103, pp. 209-215.

Kang, J. et al. "Prevention of H-Aggregates Formation in Cy5 Labeled Macromolecules", International Journal of Polymer Science, vol. 2010, Article ID 264781, pp. 1-7.

Kasha, M. et al. "The Exciton Model in Molecular Spectroscopy", Pure and Applied Chemistry, 1965, vol. 11, pp. 371-392.

Tokumaru, K. "3.1.3 Why is the energy gap between the singlet energy and the triplet energy in the n,π* excited state different from that in the π, π* excited state?", Organic Photochemical Reaction Theory, Mar. 31, 1973, pp. 79-82.

Yokoyama D., et al. "Enhancement of electron transport by horizontal molecular orientation of oxadiazole planar molecules in organic amorphous films", Applied Physics Letters, 2009, vol. 95, pp. 243303-1 to 243303-3.

Yokoyama D., et al. "Horizontal molecular orientation in vacuum-deposited organic amorphous films of hole and electron transport materials", Applied Physics Letters, 2008, vol. 93, pp. 173302-1 to 173302-3.

Yokoyama D., et al. "Horizontal orientation of linear-shaped organic molecules having bulky substituents in neat and doped vacuum-deposited amorphous films", Organic Electronics, Feb. 2009, vol. 10, Issue 1, pp. 127-137.

Tetsuya Nakagawa et al., "Thermally Activated Delayed Fluorescence Based on a Spirobifluorene Derivative and Application for Organic Light Emitting Diode", 2012, The Chemical Society of Japan.

Sae Youn Lee et al., "Molecular Design of Triazine Derivatives Having a High Up-conversion Efficiency from Triplet into Singlet Excited States and Their Application to OLEDs", 2012, The Chemical Society of Japan.

Keiro Nasu et al., "Development of Highly Efficient Electroluminescence Devices Utilizing Thermally Activated Delayed Flourescence of Spiro-structured Molecules", 2012, The Chemical Society of Japan.

Gabor Mehes et al., "Enhanced Electroluminescence Efficiency in a Spiro-Acridine Derivative through Thermally Activated Delayed Fluorescence", Angew, Chem. Int. Ed. 2012, 51, 11311-11315.

Sae Youn Lee et al., "High-efficiency organic light-emitting diodes utilizing thermally activated delayed fluorescence from triazine-based donor—acceptor hybrid molecules", Appl. Phys. Lett. 101, 093306 (2012).

Tetsuya Nakagawa et al., "Electroluminescence based on thermally activated delayed fluorescence generated by a spirobilfluorene donor—acceptor structure", Chem. Commun., 2012, 48, 9580-9582.

Tanaka Hiroyuki et al., "Efficient green thermally activated delayed fluorescence (TADF) from a phenoxazine-triphenyltriazine (PXZ-TRZ) derivative" Chem. Commun., 2012.

Qisheng Zhang et al., "Design of Efficient Thermally Activated Delayed Fluorescence Materials for Pure Blue Organic Light Emitting Diodes", J. Am. Chem. Soc., 2012.

* cited by examiner

ORGANIC ELECTROLUMINESCENCE DEVICE

The entire disclosure of Japanese Patent Application No. 2011-068758, filed Mar. 25, 2011, and U.S. Provisional Application No. 61/467,703, filed Mar. 25, 2011, is expressly incorporated by reference herein.

BACKGROUND OF THE INVENTION

1. Field of the Invention

The present invention relates to an organic electroluminescence device.

2. Description of Related Art

When voltage is applied on an organic electroluminescence device (hereinafter, referred to as an organic EL device), holes and electrons are respectively injected into an emitting layer from an anode and a cathode. The injected electrons and holes are recombined in an emitting layer to form excitons. Here, according to the electron spin statistics theory, singlet excitons and triplet excitons are generated at a ratio of 25%:75%. In the classification according to the emission principle, in a fluorescent EL device which uses emission caused by singlet excitons, the limited value of an internal quantum efficiency of the organic EL device is believed to be 25%. On the other hand, in a phosphorescent EL device which uses emission caused by triplet excitons, it has been known that the internal quantum efficiency can be improved up to 100% when intersystem crossing efficiently occurs from the singlet excitons.

A technology for extending a lifetime of a fluorescent organic EL device has recently been improved and applied to a full-color display of a mobile phone, TV and the like. However, an efficiency of a fluorescent EL device is required to be improved.

Based on such a background, a highly efficient fluorescent organic EL device using delayed fluorescence has been proposed and developed. For instance, Document 1 (International Publication No. WO2010/134350) discloses an organic EL device using TTF (Triplet-Triplet Fusion) mechanism that is one of mechanisms for delayed fluorescence. The TTF mechanism utilizes a phenomenon in which singlet excitons are generated by collision between two triplet excitons.

By using delayed fluorescence by the TTF mechanism, it is considered that an internal quantum efficiency can be theoretically raised up to 40% even in fluorescent emission. However, as compared with phosphorescent emission, the fluorescent emission is still problematic on improving efficiency. Accordingly, in order to enhance the internal quantum efficiency, an organic EL device using another delayed fluorescence mechanism has been studied.

For instance, TADF (Thermally Activated Delayed Fluorescence) mechanism is used. The TADF mechanism utilizes a phenomenon in which inverse intersystem crossing from triplet excitons to singlet excitons is generated by using a material having a small energy gap ($\Delta ST$) between the singlet level and the triplet level. An organic EL device using the TADF mechanism is disclosed in Document 2: "Expression of Highly-Efficient Thermally-Activated Delayed-Fluorescence and Application thereof to OLED" Organic EL Symposium, proceeding for the tenth meeting edited by Chihaya Adachi et al., pp. 11-12, Jun. 17-18, 2010. In the organic EL device of Document 2, a material having a small $\Delta ST$ is used as a dopant material to cause inverse intersystem crossing from the triplet level to the singlet level by heat energy. It is considered that the internal quantum efficiency can be theoretically raised up to 100% even in fluorescent emission by using delayed fluorescence by the TADF mechanism.

Although the organic EL device disclosed in Document 2 exhibits the maximum luminous efficiency at 0.01 mA/cm$^2$ of a low current density area, so-called roll-off is generated to decrease a luminous efficiency in a practically high current density area from approximately 1 mA/cm$^2$ to 10 mA/cm$^2$.

Accordingly, it is considered that many practical problems in using delayed fluorescence by the TADF mechanism are left unsolved, among which improvement in the luminous efficiency in the practically high current density area has been particularly demanded.

SUMMARY OF THE INVENTION

An object of the invention is to provide an organic EL device efficiently emitting light even in a practically high current density area using the TADF mechanism in which a material having a small $\Delta ST$ is employed.

After conducting concentrated studies in order to solve the above problem, the inventors found that the organic EL device efficiently emits light even in a high current density area by containing a first material and a second material in an emitting layer in which the first material is a compound satisfying specific conditions and the second material is a fluorescent material, and arrived at the invention.

An organic EL device according, to an aspect of the invention includes a pair of electrodes and an organic compound layer between the pair of electrodes, the organic compound layer comprising an emitting layer comprising a first material and a second material, in which the second material is a fluorescent material, singlet energy EgS(H) of the first material and singlet energy EgS(D) of the second material satisfy a relationship of a formula (1) below, and the first material satisfies a relationship of a formula (2) below in terms of a difference $\Delta ST(H)$ between the singlet energy EgS(H) and an energy gap $Eg_{77K}(H)$ at 77K.

$$EgS(H) > EgS(D) \tag{1}$$

$$\Delta ST(H) = EgS(H) - Eg_{77K}(H) < 0.3 \text{ [eV]} \tag{2}$$

In the organic EL device according to the above aspect of the invention, it is preferable that the organic EL device exhibits a delayed fluorescence ratio larger than 37.5%.

The delayed fluorescence ratio is equivalent to a ratio of a luminous intensity derived from delayed fluorescence relative to the total luminous intensity. Specifically, the delayed fluorescence ratio is obtained according to a calculation method described below.

In the above aspect of the invention, it is preferable that the organic EL device exhibits a residual intensity ratio larger than 36.0% after the elapse of 1 μs after voltage removal in a transitional EL measurement.

In the organic EL device according to the above aspect of the invention, it is preferable that a half bandwidth of a photoluminescence spectrum of the first material is 50 nm or more.

Further, in the organic EL device according to the above aspect of the invention, it is preferable that a half bandwidth of a photoluminescence spectrum of the first material is 75 nm or more.

In the organic EL device according to the above aspect of the invention, it is preferable that a difference $\Delta T$ between the energy gap $Eg_{77K}(H)$ at 77K of the first material and an energy gap $Eg_{77K}(D)$ at 77K of the second material satisfies a relationship of a formula (3) below.

$$\Delta T = Eg_{77K}(H) - Eg_{77K}(D) \geq 0.6 \text{ [eV]} \tag{3}$$

An organic EL device of the invention efficiently emits light even in a practically high current density area using the TADF mechanism in which a material having a small ΔST is employed.

DETAILED DESCRIPTION OF PREFERRED EMBODIMENT

Arrangement(s) of Organic EL Device

Figure 1:
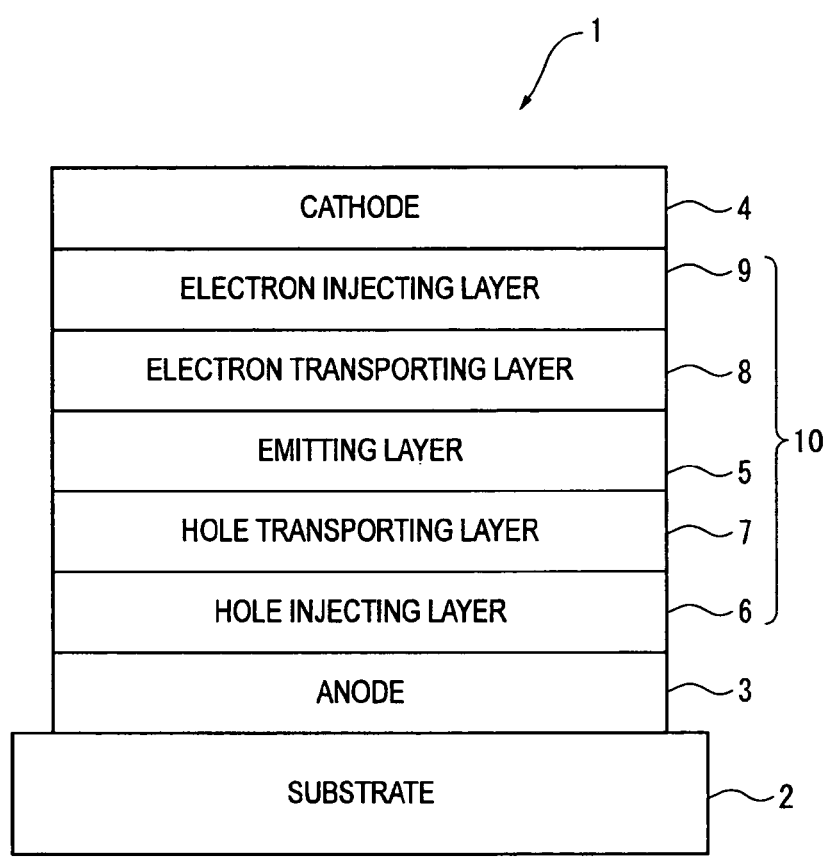
FIG. 1 schematically shows an exemplary arrangement of an organic EL device according to an exemplary embodiment of the invention.

Arrangement(s) of an organic EL device according to the invention will be described below.

The organic EL device according to the exemplary embodiment includes a pair of electrodes and an organic compound layer between the pair of electrodes. The organic compound layer includes at least one layer formed of an organic compound. The organic compound layer may include an inorganic compound.

In the organic EL device according to the exemplary embodiment, at least one layer of the organic compound layer includes an emitting layer. Accordingly, the organic compound layer may be provided by a single emitting layer. Alternatively, the organic compound layer may be provided by layers applied in a known organic EL device such as a hole injecting layer, a hole transporting layer, an electron injecting layer, an electron transporting layer, a hole blocking layer, an electron blocking layer.

The followings are representative arrangement examples of an organic EL device:
(a) anode/emitting layer/cathode;
(b) anode/hole injecting•transporting layer/emitting layer/cathode;
(c) anode/emitting layer/electron injecting•transporting layer/cathode;
(d) anode/hole injecting•transporting layer/emitting layer/electron injecting•transporting layer/cathode; and
(e) anode/hole injecting•transporting layer/emitting layer/blocking layer/electron injecting•transporting layer/cathode.

While the arrangement (d) is preferably used among the above arrangements, the arrangement of the invention is not limited to the above arrangements.

It should be noted that the aforementioned "emitting layer" is an organic compound layer generally employing a doping system and including a first material and a second material. In general, the first material promotes recombination of electrons and holes and transmits excitation energy generated by recombination to the second material. The first material is often referred to as a host material. Accordingly, the first material is referred to as the host material in descriptions hereinafter. In general, the second material receives excitation energy from the host material (the first material) to exhibit a high luminescent performance. The second material is often referred to as a dopant material. Accordingly, the second material is referred to as the dopant material in descriptions hereinafter. The dopant material is preferably a compound having a high quantum efficiency. In the exemplary embodiment, a fluorescent material is used as the dopant material.

The "hole injecting/transporting layer (or hole injecting•transporting layer) means "at least one of a hole injecting layer and a hole transporting layer while the "electron injecting/transporting layer (or electron injecting•transporting layer) means "at least one of an electron injecting layer and an electron transporting layer. Herein, when the hole injecting layer and the hole transporting layer are provided, the hole injecting layer is preferably close to the anode. When the electron injecting layer and the electron transporting layer are provided, the electron injecting layer is preferably close to the cathode.

In the exemplary embodiment, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, a blocking layer having an electron mobility that is not always high may be provided as shown in the arrangement (e) between the emitting layer and the electron transporting layer in order to prevent diffusion of excitation energy generated in the emitting layer. Thus, the organic layer adjacent to the emitting layer is not always an electron transporting layer.

FIG. 1 schematically shows an exemplary arrangement of an organic EL device according to an exemplary embodiment of the invention.

An organic electroluminescence device 1 includes a light-transmissive substrate 2; an anode 3, a cathode 4 and an organic compound layer 10 disposed between the anode 3 and the cathode 4.

The organic compound layer 10 includes an emitting layer 5 containing a host material and a dopant material. The organic compound layer 10 also includes a hole injecting layer 6 and a hole transporting layer 7 between the emitting layer 5 and the anode 3 in sequence from the anode 3. The organic compound layer 10 further includes an electron transporting layer 8 and an electron injecting layer 9 between the emitting layer 5 and the cathode 4 in sequence from the emitting layer 5.

Emitting Layer

In this exemplary embodiment, as described above, a compound satisfying specific conditions is used as the host material and the dopant material of the emitting layer. The specific conditions will be described below.

ΔST

The inventors found that the organic EL device emits light at a high efficiency in a high current density area by using a compound having a small energy gap (ΔST) between singlet energy EgS and triplet energy EgT as the host material. The ΔST(H) refers to ΔST of the host material.

From quantum chemical viewpoint, decrease in the energy difference (ΔST) between the singlet energy EgS and the triplet energy EgT can be achieved by a small exchange interaction therebetween. Physical details of the relationship between ΔST and the exchange interaction are exemplarily described in the following:

Document 3: Organic EL Symposium, proceeding for the tenth meeting edited by Chihaya Adachi et al., S2-5, pp. 11-12; and Document 4: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST; which is used as the host material in the exemplary embodiment, are compounds in which a donor element is bonded to an acceptor element in a molecule and ΔST is in a range of 0 eV or more and less than 0.3 eV in terms of electrochemical stability (oxidation-reduction stability).

An aspect of examples of the donor element is a carbazole structure and an arylamine structure.

An aspect of examples of the acceptor element is an azine ring structure, an aza-aromatic ring structure, an aza-oxygen-containing ring structure, a CN-substituted aromatic ring and a ketone-containing ring.

In the exemplary embodiment, cyclic structures including carbazole, an azine ring, an aza-aromatic ring, and an aza-oxygen-containing ring as a partial structure are also respectively referred to as the carbazole structure, the azine ring structure, the aza-aromatic ring structure, and the aza-oxygen-containing ring structure. The cyclic structures may have a substituent as needed. Examples of the substituent therefor include an alkyl group having 6 to 40 carbon atoms, a heterocyclic group having 2 to 40 carbon atoms, a trialkylsilyl group, dialkylarylsilyl group, an alkyldiarylsilyl group, a triarylsilyl group, a fluorine atom, and a cyano group. The trialkylsilyl group, the dialkylarylsilyl group, the alkyldiarylsilyl group, and the triarylsilyl group as the substituent contain at least one of an alkyl group having 1 to 30 carbon atoms and an aryl group having 6 to 30 carbon atoms. A hydrogen atom includes a deuterium atom.

Bonding between the donor element and the acceptor element means bonding by various linking groups. An aspect of examples of the linking group is a single bond, a phenylene structure and metabiphenylene structure. A compound having ΔST of less than 0.3 eV is usable as the host material in the exemplary embodiment when the compound is quantum-chemically observed based on the disclosure of the exemplary embodiment of the invention and is optimized.

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range of 0 eV to 0.2 eV.

Aggregate

Figure 2:
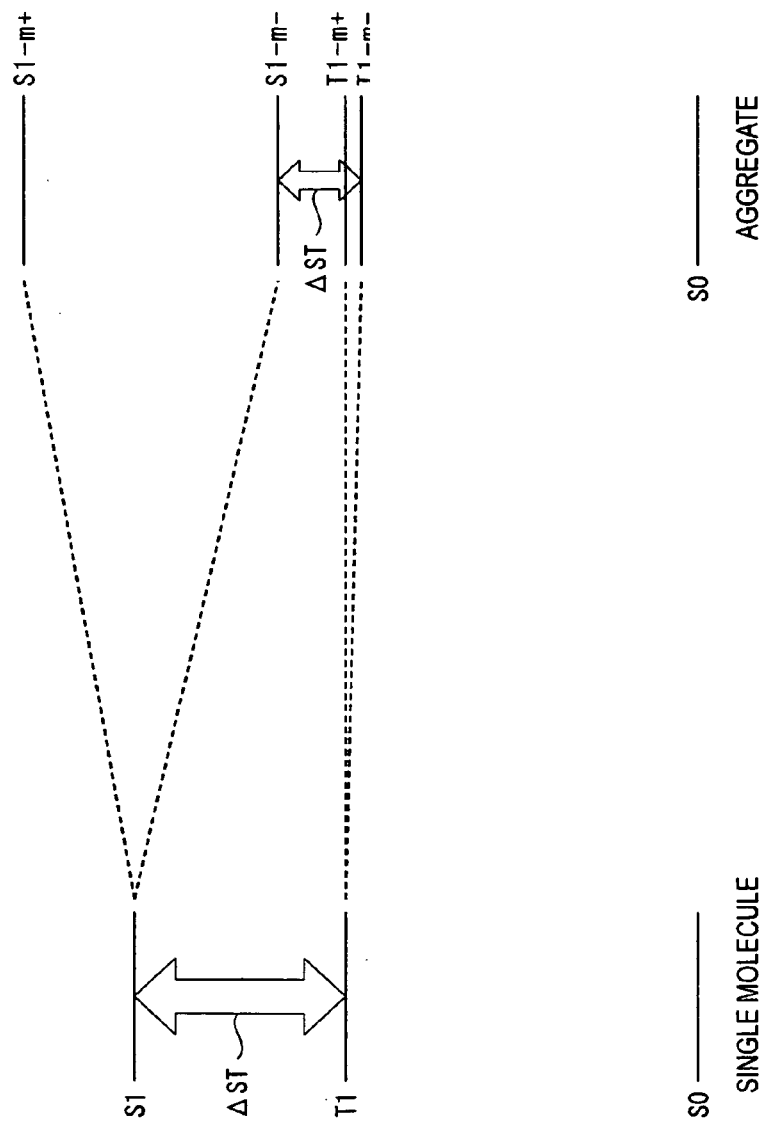
FIG. 2 shows an example of physics models with aggregate formation.

Decrease in the energy gap (ΔST) between the singlet energy EgS and the triplet energy EgT can also be achieved by aggregate formation. Herein, the aggregate does not reflect an electronic state by a single molecule, but the aggregate is provided by several molecules physically approaching each other. After the plurality of molecules approach each other, electronic states of a plurality of molecules are mixed and changed, thereby changing an energy level. A value of singlet energy is decreased, thereby decreasing a value of ΔST. The decrease in the value of ΔST by the aggregate formation can also be explained by Davydov splitting model showing that two molecules approach each other to change electronic states thereof (see FIG. 2). As shown in Davydov splitting model, it is considered that change of the electronic states by two molecules different from change of an electronic state by a single molecule is brought about by two molecules physically approaching each other. A singlet state exists in two states represented by $S1\text{-}m^+$ and $S1\text{-}m^-$. A triplet state exists in two states represented by $T1\text{-}m^+$ and $T1\text{-}m^-$. Since $S1\text{-}m^-$ and $T1\text{-}m^-$ showing a lower energy level exist, ΔST representing a gap between $S1\text{-}m^-$ and $T1\text{-}m^-$ becomes smaller than that in the electronic state by a single molecule.

The Davydov splitting model is exemplarily described in the following:

Document 5: J. Kang, et al, International Journal of Polymer Science, Volume 2010, Article ID 264781;

Document 6: M. Kasha, et al, Pure and Applied Chemistry, Vol. 11, p 371, 1965; and Document 7: S. Das, et al, J. Phys. Chem. B. vol. 103, p 209, 1999.

The inventors found usage of sublevels of a singlet state and a triplet state of a compound easily forming an aggregate in a thin film, and consequent possibility of promotion of inverse intersystem crossing by molecules and aggregates in the thin film.

For instance, a compound having a large-half bandwidth of a photoluminescence spectrum is considered to easily form an aggregate in a thin film of the compound. A relationship between the half bandwidth of the photoluminescence spectrum and easy formability of the aggregate can be estimated as follows.

In a compound having a property of typically existing as a single molecule without forming an aggregate, a vibrational level is less recognized in the singlet state, so that a narrow half bandwidth of the photoluminescence spectrum is observed. For instance, CBP exhibits a property to typically exist as a single molecule, in which a half bandwidth of a photoluminescence spectrum is relatively narrow as much as about 50 nm.

On the other hand, in the compound easily forming the aggregate, a plurality of molecules electronically influence each other, whereby a lot of vibrational levels exist in the singlet state. As a result, since the vibrational levels of the singlet state are often relaxed to the ground state, the half bandwidth of the photoluminescence spectrum is increased.

Such a compound easily forming the aggregate is expected to have a lot of vibrational levels even in a triplet state. Consequently, it is speculated that ΔST in relation to heat is decreased through the sublevels to promote the inverse intersystem crossing, since a lot of sublevels exist between the singlet state and the triplet state.

It should be noted that the aggregate according to the exemplary embodiment means that a single molecule forms any aggregate with another single molecule. In other words, a specific aggregate state is not shown in the exemplary embodiment. An aggregate state of an organic molecule is probably formable in various states in a thin film, which is different from an aggregate state of an inorganic molecule.

TADF Mechanism

As described above, when $\Delta ST(H)$ of the organic material is small, inverse intersystem crossing from the triplet level of the host material to the singlet level thereof is easily caused by heat energy given from the outside. Herein, an energy state conversion mechanism to perform spin exchange from the triplet state of electrically excited excitons within the organic EL device to the singlet state by inverse intersystem crossing is referred to as TADF Mechanism.

In the exemplary embodiment, since the material having a small $\Delta ST(H)$ is used as the host material, inverse intersystem crossing from the triplet level of the host material to the singlet level thereof is easily caused by heat energy given from the outside.

Figure 3:
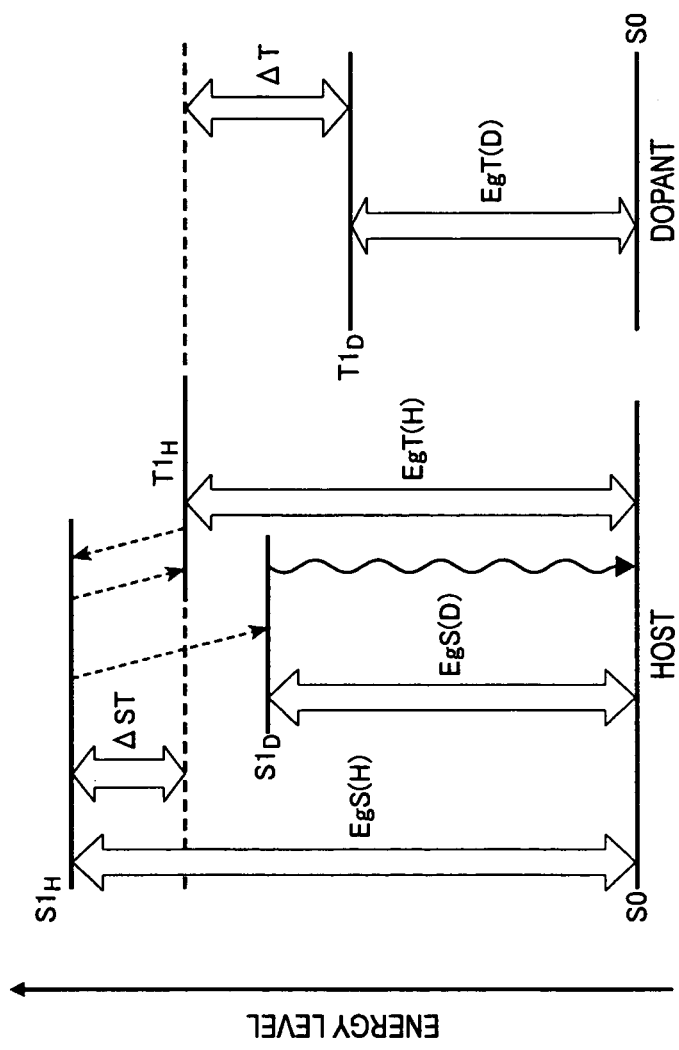
FIG. 3 shows a relationship in energy level between a host material and a dopant material in an emitting layer.

FIG. 3 shows a relationship in energy level between the host material and the dopant material in the emitting layer. In FIG. 3, S0 represents a ground state, $S1_H$ represents a lowest singlet state of the host material, $T1_H$ represents a lowest triplet state of the host material, $S1_D$ represents a lowest singlet state of the dopant material, and $T1_D$ represents a lowest triplet state of the dopant material. As shown in FIG. 3, a difference between $S1_H$ and $T1_H$ corresponds to $\Delta ST(H)$, a difference between $S1_H$ and S0 corresponds to EgS(H), a difference between $S1_D$ and S0 corresponds to EgS(D) corresponds to EgS(D), and a difference between $T1_H$ and $T1_D$ corresponds to $\Delta T$. A dotted-line arrow shows energy transfer between the respective excited states in FIG. 3.

As described above, a material having a small $\Delta ST$ is selected as the compound for the host material in the exemplary embodiment. This is because the material having a small $\Delta ST(H)$ is considered to easily cause inverse intersystem crossing from the triplet excitons generated in the lowest triplet state $T1_H$ to the lowest singlet state $S1_H$ of the host material by heat energy. Due to the small $\Delta ST(H)$, inverse intersystem crossing is easily caused, for instance, even around a room temperature. When the inverse intersystem crossing is thus easily caused, a ratio of energy transfer from the host material to the lowest singlet state $T1_D$ of the fluorescent dopant material is increased by Förster transfer, resulting in improvement in a luminous efficiency of a fluorescent organic EL device.

In other words, use of the compound having a small $\Delta ST(H)$ as the host material increases emission by the TADF mechanism, so that a delayed fluorescence ratio becomes large. When the delayed fluorescence ratio is large, a high internal quantum efficiency is achievable. It is considered that the internal quantum efficiency can be theoretically raised up to 100% even by using delayed fluorescence by the TADF mechanism.

Figure 4:
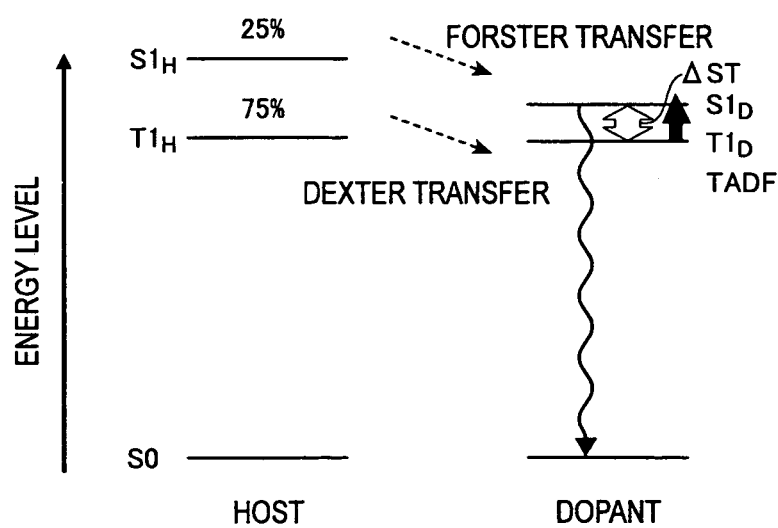
FIG. 4 shows a relationship in energy level between the host material and the dopant material in the emitting layer.

FIG. 4 shows a relationship in energy level between the host material and the dopant material in the emitting layer in the TADF mechanism described in Document 1. In FIG. 4, S0, $S1_H$, $T1_H$, $S1_D$, and $T1_D$ represent the same as those in FIG. 3. A dotted-line arrow shows energy transfer between the respective excited states. As shown in FIG. 4, a material having a small $\Delta ST(D)$ is used as the dopant material in the TADF mechanism described in Document 1. Accordingly, energy is transferred from the lowest triplet state $T1_H$ of the host material to the lowest triplet state $T1_D$ of the dopant material by Dexter transfer. Further, inverse intersystem crossing from the lowest triplet state $T1_D$ to the lowest singlet state $S1_D$ of the dopant material is possible by heat energy. As a result, fluorescent emission from the lowest triplet state $T1_D$ of the dopant material can be observed. It is considered that the internal quantum efficiency can be theoretically raised up to 100% also by using delayed fluorescence by the TADF mechanism.

As described in Document 2, the inventors employ a fluorescent compound having a small $\Delta ST(H)$ in a host-dopant system.

The inventors used a fluorescent compound having a small $\Delta ST(H)$ as the host material because of the following detailed reasons.

First, considering conversion of energy states on the dopant material by the TADF mechanism, the dopant material has a relatively high singlet energy for fluorescent emission and triplet energy approximately equivalent to the singlet energy. In order to efficiently trap the triplet energy within the emitting layer, it is necessary to select a host material having larger triplet energy. If a typical organic material usually having a large $\Delta ST$ is used as the host material, the singlet energy of the host material, i.e., an energy gap between a HOMO level and a LUMO level becomes extremely large. As a result, an energy gap between the host material and a carrier transporting layer adjacent to the emitting layer becomes large, so that injection of carriers to the emitting layer is considered to become difficult. Accordingly, the inventors consider that conversion of the energy states by the TADF mechanism is preferably performed on the host material, whereby the carriers are advantageously injected to the emitting layer and are easily balanced in the entire organic EL device.

Secondly, the inventors believe it possible to suppress decrease in a luminous efficiency caused by Triplet-Triplet-Annihilation in a high current density area by using the fluorescent compound having a small $\Delta ST(H)$ as the host material. Herein, Triplet-Triplet-Annihilation (hereinafter, referred to as TTA) is a physical phenomenon in which long-life triplet excitons generated on a molecule are adjacent to each other at a high density to collide with each other and is thermally deactivated.

The inventors believe it possible to suppress decrease in the luminous efficiency in the high current density area to some extent in the host-dopant system in which the triplet energy is difficult to transit from the host material to the dopant material. In the exemplary embodiment, the compound having a small $\Delta ST$ is used as the host material of the emitting layer. After inverse intersystem crossing from a triplet excited level of the host material to a singlet excited level thereof by the TADF mechanism, energy is transferred to a singlet excited level of the dopant material. Accordingly, the generated triplet excitons are kept in a triplet excited state on the host material whose abundance ratio is high in the emitting layer. On the other hand, if the compound having a small $\Delta ST$ is used as the dopant material in the emitting layer, the generated triplet excitons are kept in a triplet excited state on the dopant material whose abundance ratio is extremely low in the emitting layer. In other words, the inventors believe it preferable to design a system that avoids concentration of triplet excited state on the dopant material in driving the organic EL in the high current density area. Accordingly, in the exemplary embodiment, the inventors employ the material having a small $\Delta ST(H)$ as the host material.

Thirdly, a material having a high emission quantum efficiency can be easily selected as the dopant material by using a material causing inverse intersystem crossing from the triplet level to the singlet level as the host material. As a result, emission of the singlet excitons is quickly relaxed after energy transfer thereof to the dopant material, so that energy quenching in the high current density area is suppressible. In the host-dopant system in a fluorescent device, generally, the host material has a carrier transporting function and an exciton generating function and the dopant material has an emission function. This system is for separating the carrier transporting function and the emission function of the emitting layer. Accordingly, effective organic EL emission is promoted by doping a small amount of a dopant material having a high emission quantum efficiency into the emitting layer. The emitting layer according to the exemplary embodiment is required to have a function to cause inverse intersystem crossing by the TADF function in addition to a typical function of the emitting layer. By requiring the host material to have the function to cause inverse intersystem crossing by the TADF function, the inventors increased choices of the dopant material having a high emission quantum efficiency which largely contributes to the luminous efficiency of the organic EL. With this arrangement, a fluorescent dopant material typically known as being highly efficient can be selected. Relationship Between EgT and $Eg_{77K}$ In this exemplary embodiment, the compound having ΔST of a predetermined value or less is used. The aforementioned triplet energy EgT is different from a typically defined triplet energy. Such a difference will be described below.

For general measurement of the triplet energy, a target compound to be measured is dissolved in a solvent to form a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. The triplet energy is calculated by a predetermined conversion equation based on a wavelength value at an intersection of the tangent and the abscissa axis.

As described above, the compound for the host material in the exemplary embodiment has a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish emission from the singlet state from emission from the triplet state, the value of the triplet energy is basically considered dominant.

Accordingly, in order to distinguish the triplet energy EgT in the exemplary embodiment from the typical triplet energy EgT in a strict meaning although the measurement method is the same, the triplet-energy EgT in the exemplary embodiment is defined as follows. A target compound to be measured is dissolved in a solvent to form a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. Energy is calculated as an energy gap $Eg_{77K}$ by a predetermined conversion equation based on a wavelength value at an intersection of the tangent and the abscissa axis. ΔST is defined as a difference between the singlet energy EgS and the energy gap $Eg_{77K}$. Accordingly, ΔST(H) is represented by the formula (1).

The triplet energy measured in a solution state may include an error by interaction between the target molecule and the solvent. Accordingly, as an ideal condition, a measurement in a thin film state is desired in order to avoid the interaction between the target molecule and the solvent. In this exemplary embodiment, the molecule of the compound used as the host material exhibits a photoluminescence spectrum having a broad half bandwidth in a solution state, which strongly implies aggregate formation also in the solution state. Accordingly, the solution state is considered to be under the same conditions as in a thin film state. Consequently, in this exemplary embodiment, a measurement value of the triplet energy in the solution state is used.

Singlet Energy EgS

The singlet energy EgS in the exemplary embodiment is defined based on calculation by a typical method. Specifically, the target compound is evaporated on a quartz substrate to prepare a sample. An absorption spectrum (ordinate axis: absorbance, abscissa axis: wavelength) of the sample is measured at a normal temperature (300K). A tangent is drawn to the rise of the absorption spectrum on the long-wavelength side. The singlet energy EgS is calculated by a predetermined conversion equation based on the tangent and the wavelength value at the intersection. EgS in aggregate formation corresponds to an energy gap between S1-*m*- and the ground state S0 in the Davydov splitting model.

The calculation of the singlet energy EgS and the energy gap $Eg_{77K}$ will be described in detail later.

Delayed Fluorescence Ratio

It was found that a delayed fluorescence ratio according to the organic EL device of the exemplary embodiment exceeds the theoretical upper-limit of a delayed fluorescence ratio (TTF ratio) of a case where it is assumed that delayed fluorescence is generated only by the TTF mechanism. In other words, according to the exemplary embodiment, an organic EL device having a higher internal quantum efficiency is achievable.

The delayed fluorescence ratio is measurable by a transitional EL method. The transitional EL method is for measuring reduction behavior (transitional property) of EL emission after pulse voltage applied on the device is removed. EL luminous intensity is classified into a luminescence component from singlet excitons generated in first recombination and a luminescence component from singlet excitons generated through triplet excitons. Since lifetime of the singlet excitons generated in the first recombination is very short at a nano-second order, EL emission is rapidly reduced after removal of pulse voltage.

On the other hand, since delayed fluorescence provides emission from singlet excitons generated through long-life triplet excitons, EL emission is gradually reduced. Thus, since there is a large difference in time between emission from the singlet excitons generated in the first recombination and emission from the singlet excitons derived from the triplet excitons, a luminous intensity derived from delayed fluorescence is obtainable. Specifically, the luminous intensity can be determined by the following method.

Figure 5:
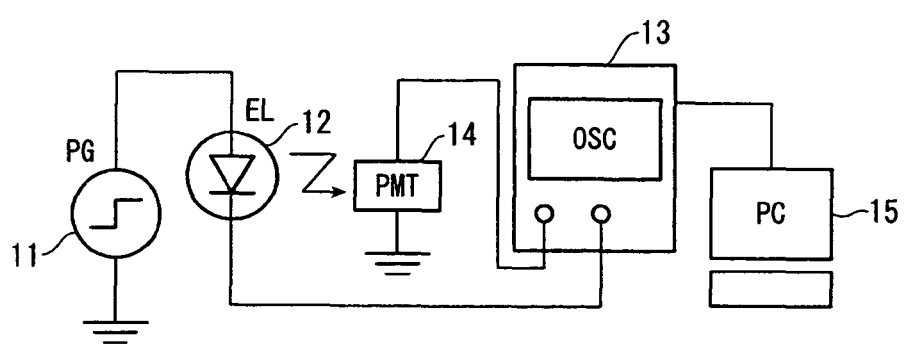
FIG. 5 shows a measurement system of transitional EL waves.

Transitional EL waveform is measured as follows (see FIG. 5). Pulse voltage waveform outputted from a voltage pulse generator (PG) 11 is applied on an organic EL device (EL) 12. The applied voltage waveform is loaded in an oscilloscope (OSC) 13. When pulse voltage is applied on the organic EL device 12, the organic EL device 12 generates pulse emission. This emission is loaded in the oscilloscope (OSC) 13 through a photomultiplier (PMT) 14. The voltage waveform and the pulse emission are synchronized and loaded in a personal computer (PC) 15.

The ratio of luminous-intensity derived from delayed fluorescence is defined as follows based on analysis of the transitional EL waveform. It should be noted that a formula to calculate a TTF ratio described in International Publication No. WO2010/134352 may be used for calculation of the ratio of luminous intensity derived from delayed fluorescence.

It is considered that a delayed fluorescence component defined in the exemplary embodiment includes thermally activated delayed fluorescence (TADF mechanism) recited in the exemplary embodiment in addition to the luminescence component derived from TTF. For this reason, in the exemplary embodiment, a ratio of the delayed fluorescence component calculated according to the following formula (4) is referred to as a delayed fluorescence ratio, not as a TTF ratio.

The delayed fluorescence ratio is calculated according to the formula (4).

$$\frac{1}{\sqrt{I}} \propto A + \gamma \cdot t \tag{4}$$

In the formula (4), I represents luminous intensity derived from delayed fluorescence. A represents a constant. The measured transitional EL waveform data is fit in the formula (4) to obtain the constant A. Here, a luminous intensity $1/A^2$ at the time t=0 when pulse voltage is removed is defined as the ratio of luminous intensity derived from delayed fluorescence.

Figure 6A:
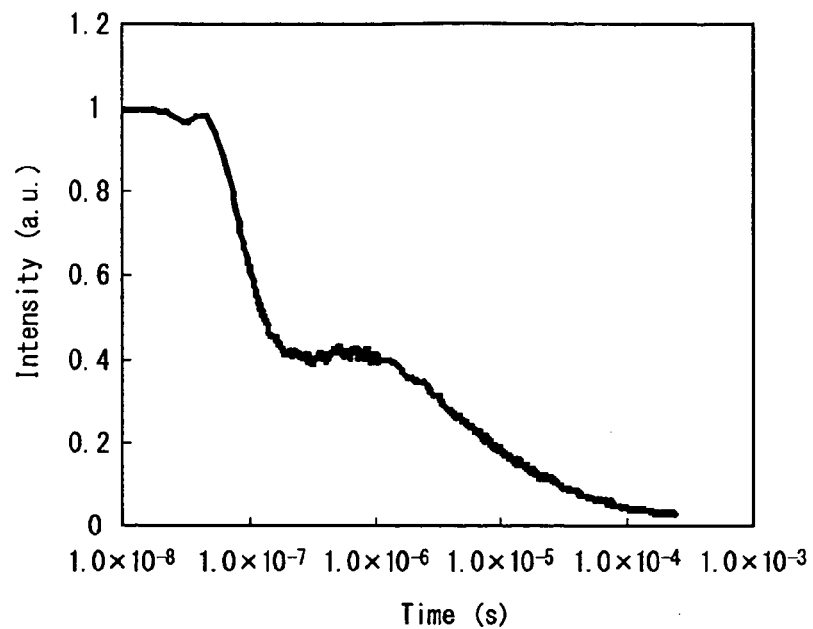
FIG. 6A shows a measurement method of a ratio of luminous intensities derived from delayed fluorescence and is a graph showing time-varying luminous intensities of the EL device.

A graph of FIG. 6A shows a measurement example where a predetermined pulse voltage is applied on the organic EL device and then the pulse voltage is removed and shows time-varying luminous intensities of the organic EL device.

The pulse voltage was removed at the time of about $3 \times 10^{-8}$ seconds in the graph of FIG. 6A. In the graph of FIG. 6A, the luminous intensity when the voltage is removed is defined as 1.

After rapid reduction before the elapse of about $2 \times 10^{-7}$ seconds after the voltage removal, a gradual reduction component appears.

Figure 6B:
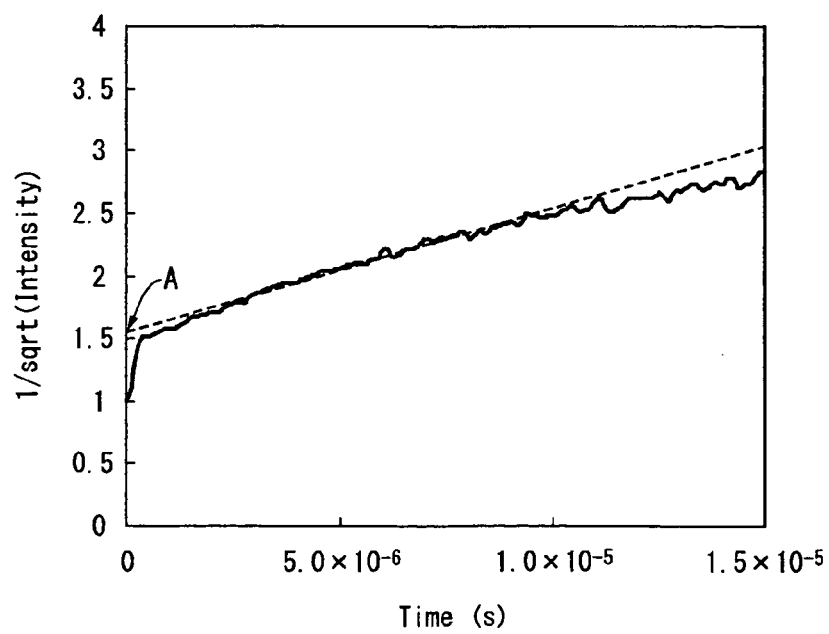
FIG. 6B shows a measurement method of a ratio of luminous intensities derived from delayed fluorescence and is a graph showing time-varying inverse square root of luminous intensities.

In the graph of FIG. 6B, the voltage removal time is a starting point and the inverse square root of luminous intensity before the elapse of $1.5 \times 10^{-5}$ seconds after voltage removal is plotted. Fitting is conducted as follows.

A value at an intersection A of the ordinate axis and the linear line extended to the starting point is 1.55. Accordingly, the ratio of luminous intensity derived from the delayed fluorescence obtained from the transitional EL waveform is $1/(1.55)^2 = 0.41$, which means 41% of the luminous intensity was derived from the delayed fluorescence. In other words, the ratio of luminous intensity exceeds 37.5%, i.e., the supposed theoretical upper-limit of the TTF ratio.

The luminous intensity derived from the delayed fluorescence obtained from the transitional EL waveform is variable in accordance with measurement temperatures. Such a phenomenon is considered to be inherent mostly in fluorescent emission by the TADF mechanism The luminous intensity is preferably fitted in a linear line by the method of least squares. In this case, the luminous intensity before the elapse of $10^{-5}$ seconds is preferably fitted.

Figure 7:
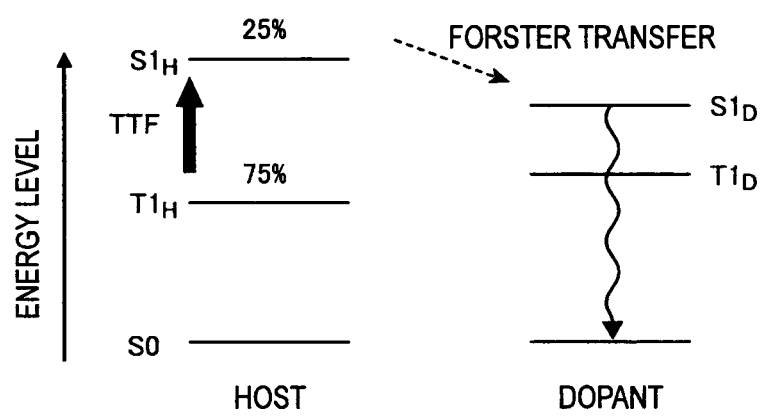
FIG. 7 shows a relationship in energy level between the host material and the dopant material in the emitting layer.

The TTF mechanism having an emission mechanism by delayed fluorescence will be described using FIG. 7. FIG. 7 shows a relationship in energy level between the host material and the dopant material in an organic EL device using the TTF mechanism. In FIG. 7, S0, $S1_H$, $T1_H$, $S1_D$ and $T1_D$ represent the same as those in FIG. 3. An arrow shows energy transfer between the respective excited states in FIG. 7.

As described above, the TTF mechanism utilizes a phenomenon in which singlet excitons are generated by collision between two triplet excitons. As shown in FIG. 7, it is preferable that the lowest triplet state $T1_H$ of the host material is lower than the lowest triplet state $T1_D$ of the dopant material, so that triplet excitons concentrate on molecules of the host material. The triplet excitons efficiently collide with each other in accordance with increase in the density of the triplet excitons, whereby the triplet excitons are partially changed into singlet excitons. The lowest singlet state $S1_H$ of the host material generated by the TTF mechanism is immediately transferred to the lowest singlet state $S1_D$ of the dopant material by Förster transfer, so that the dopant material emits fluorescence.

The theoretical upper-limit of the TTF ratio can be obtained as follows.

According to S. M. Bachilo et al. (J. Phys. Chem. A, 104, 7711 (2000)), assuming that high-order excitons such as quintet excitons are quickly returned to triplet excitons, triplet excitons (hereinafter abbreviated as $^3A^*$) collide with one another when the density thereof is increased, whereby a reaction shown by the following formula (5) occurs. In the formula, $^1A$ represents the ground state and $^1A^*$ represents the lowest singlet excitons.

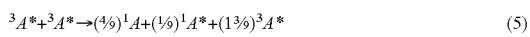

$$^3A^* + ^3A^* \rightarrow (4/9)^1A + (1/9)^1A^* + (13/9)^3A^* \tag{5}$$

In short,

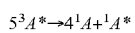

$$5 \, ^3A^* \rightarrow 4 \, ^1A + ^1A^*$$

It is expected that, among triplet excitons initially generated, which account for 75%, one fifth thereof (i.e., 20%) is changed to singlet excitons.

Accordingly, the amount of singlet excitons which contribute to emission is 40%, which is a value obtained by adding 15% (75% × (1/5) = 15%) to 25%, which is the amount ratio of initially generated singlet excitons.

At this time, a ratio of luminous intensity derived from TTF (TTF ratio) relative to the total luminous intensity is 15/40, i.e., 37.5%. Thus, it is recognized that the delayed fluorescence ratio of the organic EL device according to the exemplary embodiment exceeds the theoretical upper-limit of only the TTF ratio.

Residual Intensity Ratio in 1 μs

A method for relatively measuring an amount of delayed fluorescence is exemplified by a method for measuring a residual intensity in 1 μs. The residual intensity in 1 μs is defined as a ratio of a luminous intensity after the elapse of 1 μs after removal of a pulse voltage measured by a transitional EL method to a voltage at the time of the removal of the pulse voltage. The relative amount of delayed fluorescence can be estimated based on reduction behavior of EL emission after the removal of the pulse voltage measured by the transitional EL method. The residual intensity ratio in 1 μs can be obtained by reading luminous intensity at the time of 1.0 μs in the graph of FIG. 6A.

The residual intensity ratio in 1 μs is preferably larger than 36.0%, more preferably 38.0 or more.

Dopant Properties

A preferable dopant in the exemplary embodiment has properties to emit fluorescence and to have a large speed constant of radiational transition. In this arrangement, singlet excitons electrically excited on the host material, singlet excitons generated by the TADF mechanism and the like are transferred to singlet excitons of the dopant material by Förster energy transfer and the dopant material immediately emits light. In other words, fluorescent emission is possible through the above energy transition before triplet excitons on the host material causes TTA, by which decrease in an efficiency in the high current area is likely to be considerably improved.

It is preferable to select a dopant material having a fluorescence lifetime of 5 ns or less, more preferably 2 ns or less as the dopant material having a large speed constant of radiational transition in the exemplary embodiment. A fluorescence quantum efficiency of the dopant material is preferably 80% or more in a solution. The fluorescence quantum efficiency can be obtained by measuring the dopant material in a range of $10^{-5}$ to $10^{-6}$ mol/l of a concentration in a toluene solution using Absolute PL Quantum Yield Measurement System C9920-02 manufactured by HAMAMATSU PHOTONICS K.K.

It is also expected by measuring an EL spectrum of the device and confirming a luminescence component of a material other than the dopant material is 1/10 or less of the luminescence component of the dopant that the dopant material has a large speed constant of radiational transition.

Relationship Between Emitting Layer and Electron Transporting Layer

When $\Delta ST(H)$ of the host material is small, the energy gap between the host material and the electron transporting layer adjacent thereto is small, so that the electrons are likely to be injected into the emitting layer. As a result, carrier balance is easily obtainable to decrease roll-off.

Relationship between Emitting Layer and Hole Transporting Layer

When an ionization potential of the hole transporting layer is represented by $IP_{HT}$, $IP_{HT} \leq 5.7$ eV is preferable. With this arrangement, balance between the electrons and the holes can be enhanced. The ionization potential can be obtained, for instance, by measuring the material in a form of a thin film using a photoelectron spectroscopy (AC-3: manufactured by RIKEN KEIKI Co., Ltd.).

Relationship in Singlet Energy Between Host Material and Dopant Material

In the exemplary embodiment, the dopant material is a fluorescent dopant material. A compound used as the host material and a compound used as the dopant material satisfy a relationship represented by the formula (2) in terms of the singlet energy.

When such a relationship is satisfied, energy of the singlet excitons initially generated on the host material and the singlet excitons derived from the delayed fluorescence is easily transferred to the dopant material. Consequently, the dopant efficiently emits fluorescence.

$\Delta n$

The inventors found that one way to reduce $\Delta ST$ is to use the compound forming the aggregate and that the compound having a large $\Delta n$ easily forms the aggregate in a film of the compound. Herein, $\Delta n$ is a value representing the largest difference between the refractive index $n_Z$ perpendicular to the silicon substrate surface and the refractive index $n_X$ parallel to the silicon substrate surface in an area where a reflectivity to be observed simultaneously with a refractivity is not observed, in the spectroscopic ellipsometry measurement (measurement range: 200 nm to 1000 nm).

A relationship between $\Delta n$ and easy formability of the aggregate is estimated as follows.

When a large difference is generated between a refractive index n in a vertical direction z relative to the silicon substrate and a refractive index n in a parallel direction x relative to the silicon substrate, it is considered that molecules exist with a certain regularity in a thin film state. In other words, the compound used as the host material in the exemplary embodiment is expected to have a predetermined value of $\Delta n$ while forming the aggregate in the thin film state to exhibit a certain regularity.

On the other hand, a compound having an extremely small $\Delta n$ (e.g., CBP and $Alq_3$) exists in an amorphous state in which molecules have no regularity in a thin film state.

The relationship between $\Delta n$ and easy formability of the aggregate is described in the following:

Document 8: D. Yokoyama et al., Org. Electron. 10, 127-137 (2009);

Document 9: D. Yokoyama et al., Appl. Phys. Lett. 93, 173302 (2008); and

Document 10: D. Yokoyama et al., Appl. Phys. Lett. 95, 243303 (2009).

Figure 8A:
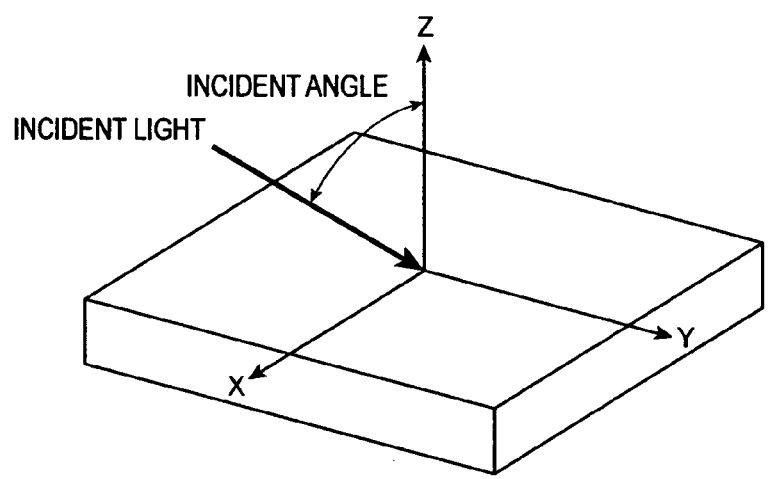
FIG. 8A schematically shows an incident angle of an incident light from a light source as an example of spectroscopic ellipsometry measurement.
Figure 8B:
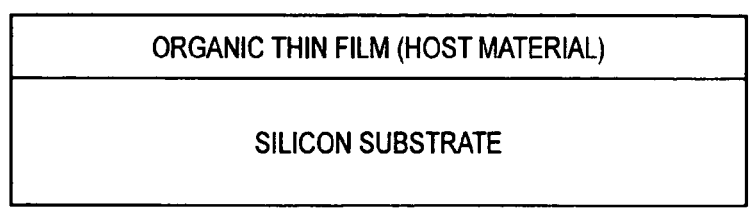
FIG. 8B shows a cross section of an organic thin film on a silicon substrate (a measurement target) as an example of the spectroscopic ellipsometry measurement.

$\Delta n$ can be calculated based on the refractive index of each compound measured by the spectroscopic ellipsometry method. The spectroscopic ellipsometry method is a measurement method of an optical constant (i.e., a refractive index n and an extinction coefficient k) and a thickness of a thin film. For instance, a variable-incident-angle high-speed spectroscopic ellipsometer (M*-2000D: manufactured by J. A. Woollam Co., Inc.) is usable. FIGS. 8A and 8B show an example of spectroscopic ellipsometry measurement. FIG. 8A shows an incident angle of an incident light from a light source. FIG. 8B shows a cross section of an organic thin film (a measurement target) on a silicon substrate.

Each compound is evaporated on the silicon substrate (Si (100)) to form a 100-nm organic thin film. Using the variable-incident-angle high-speed spectroscopic ellipsometer (M-2000D: manufactured by J. A. Woollam Co., Inc.), ellipsometric parameters $\psi$ and $\Delta$ are measured at every five degrees in a range of 45 degrees to 80 degrees of an incident angle and at every 1.6 nm in a range of 200 nm to 1000 nm of a wavelength. The obtained parameters are analyzed together using an analysis software WVASE32 (manufactured by J. A. Woollam Co., Inc) to examine optical anisotropy of the film. The anisotropy of the optical constant (i.e., the refractive index n and the extinction coefficient k) of the film reflects the anisotropy of molecular orientation in the film. The measurement method and the analysis methods are described in detail in the above Documents 8 to 10.

$\Delta n$ can be obtained as a difference between the refractive index n in the perpendicular direction z relative to the silicon substrate and the refractive index n in the parallel direction x relative to the silicon substrate. The perpendicular direction z and the parallel direction x relative to the silicon substrate are shown in FIG. 8A.

Half Bandwidth

A half bandwidth represents a width of an emission spectrum when a luminous intensity becomes half relative to the maximum luminous intensity of the emission spectrum. The inventors found that a host material having 50 nm or more of a half bandwidth of a photoluminescence spectrum is a material easily forming an aggregate state and easily causing inverse intersystem crossing in a thin film. Accordingly, the TADF mechanism easily works in the host material having 50 nm or more of the half bandwidth, of the photoluminescence spectrum. Particularly preferably, the half bandwidth of the photoluminescence spectrum of the host material is 75 nm or more.

$\Delta T$

It is preferable that a difference $\Delta T$ between triplet energy $Eg_{77K}(H)$ of the host material and triplet energy $Eg_{77K}(D)$ of the dopant material satisfies a relationship represented by the formula (3). $\Delta T$ is more preferably 0.8 eV or more, further preferably 1.0 eV or more.

When $\Delta T$ satisfies the relationship represented by the formula (3), energy of the triplet excitons generated by recombination on the host material becomes difficult to transfer to the triplet level of the dopant material, and thermal deactivation of the triplet excitons becomes difficult. Consequently, the dopant efficiently emits fluorescence.

Compound(s) of Emitting Layer

Compounds satisfying the relationships represented by the formulae (1) and (2) and used as the host material and the dopant material are as follows.

Host Material

Examples of the host material include a carbazole derivative, a biscarbazole derivative, an indolocarbazole derivative, an acridine derivative, an oxazine derivative, a pyrazine derivative, a pyrimidine derivative, a triazine derivative, a dibenzofuran derivative, and a dibenzothiophene derivative. These derivatives may have a substituent as needed.

Examples of the substituent therefor include an alkyl group having 6 to 40 carbon atoms, a heterocyclic group having 2 to 40 carbon atoms, a trialkylsilyl group, dialkylarylsilyl group, an alkyldiarylsilyl group, a triarylsilyl group, a fluorine atom, and a cyano group. The trialkylsilyl group, the dialkylarylsilyl group, the alkyldiarylsilyl group, and the triarylsilyl group as the substituent contain at least one of an alkyl group having 1 to 30 carbon atoms and an aryl group having 6 to 30 carbon atoms. A hydrogen atom includes a deuterium atom.

The host material is preferably a compound including bonding between at least one selected from a carbazole structure, a biscarbazole structure, an indolocarbazole structure, and an acridine structure and at least one selected from an oxazine structure, a pyrazine structure, a pyrimidine structure, a triazine structure, and a dibenzofuran structure.

Bonding between these structures means bonding by various linking groups. An aspect of examples of the linking group is a single bond, a phenylene structure and metabiphenylene structure.

In the exemplary embodiment, the carbazole structure, the indolocarbazole structure, the acridine structure, the oxadine structure, the pyrazine structure, the pyrimidine structure, the triazine structure, and the dibenzofuran structure respectively refer to cyclic structures containing indolocarbazole, acridine, oxadine, pyrazine, pyrimidine, triazine, and dibenzofuran as a partial structure.

The carbazole structure, the biscarbazole structure, the indolocarbazole structure, the acridine structure, the oxazine structure, the pyrazine structure, the pyrimidine structure, the triazine structure, and the dibenzofuran structure may have a substituent as needed.

Examples of the substituent therefor include an alkyl group having 6 to 40 carbon atoms, a heterocyclic group having 2 to 40 carbon atoms, a trialkylsilyl group, dialkylarylsilyl group, an alkyldiarylsilyl group, a triarylsilyl group, a fluorine atom, and a cyano group. The trialkylsilyl group, the dialkylarylsilyl group, the alkyldiarylsilyl group, and the triarylsilyl group as the substituent contain at least one of an alkyl group having 1 to 30 carbon atoms and an aryl group having 6 to 30 carbon atoms. A hydrogen atom includes a deuterium atom.

Since the most material is a compound in which a donor element is bonded to an acceptor element in a molecule, the host material is preferably selected from compounds represented by the following formulae (101) and (102).

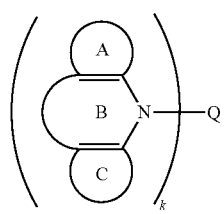

(101)

In the formula (101): rings A, B, and C each are a substituted or unsubstituted five- to seven-membered ring including as a ring-forming atom an atom selected from a carbon atom, a nitrogen atom, an oxygen atom, a sulfur atom, and a silicon atom; the ring A is fused with the ring B and the ring C is fused with the ring B; the ring C may be fused with an additional ring; Q represents a group represented by a formula (103) below; and k is 1 or 2.

(103)

In the formula (103): at least one of $Y^1$ to $Y^6$ is a carbon atom to be bonded to L; one to three of $Y^1$ to $Y^6$ are a nitrogen atom(s); the rest of $Y^1$ to $Y^6$ of the carbon atom bonded with L or the nitrogen atom is $CAr^1$; $Ar^1$ is a substituted or unsubstituted aromatic hydrocarbon group; when the formula (103) include a plurality of $CAr^1$, $Ar^1$ is mutually the same or different; and L represents a single bond or a linking group.

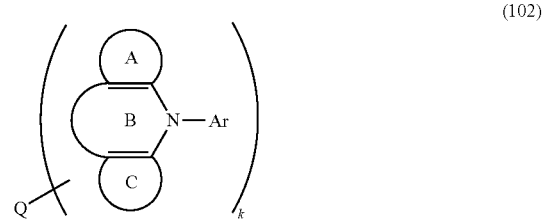

(102)

In the formula (102): the ring A, the ring B, the ring C, Q, and k represent the same as those in the formula (101); and Ar is a substituted or unsubstituted aromatic hydrocarbon group.

Compounds in which the ring C in the formulae (101) is fused with the additional ring are respectively represented by the following formulae (101A) and (101B). Compounds in which the ring C in the formulae (102) is fused with the additional ring are respectively represented by the following formulae (102A) and (102B).

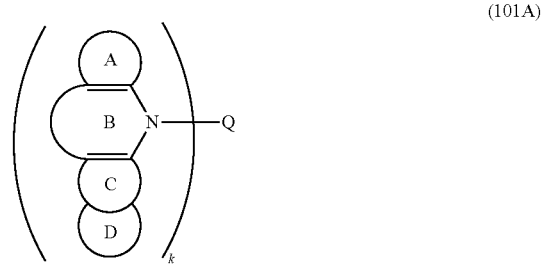

(101A)

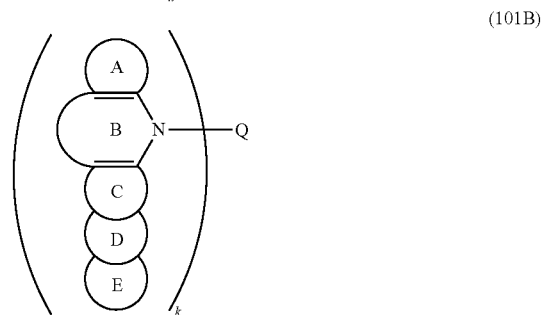

(101B)

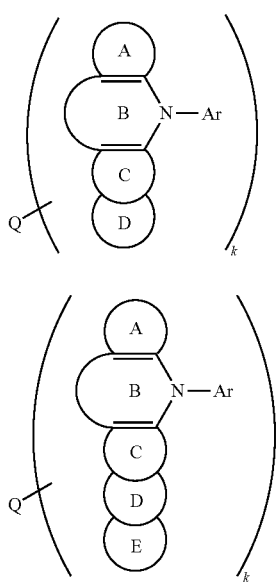

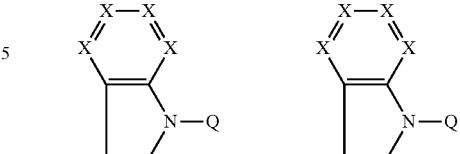

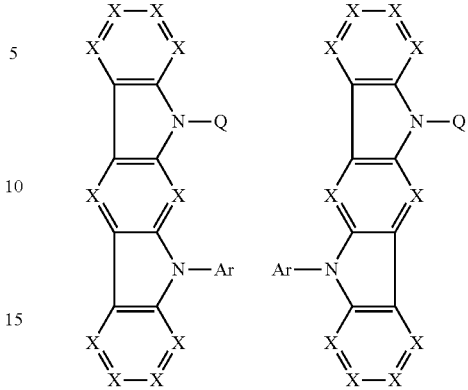

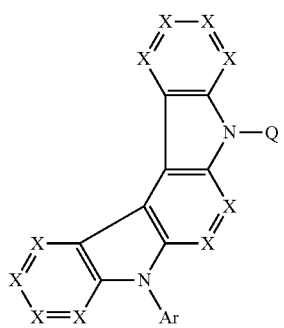

In the each formula: the ring A, the ring B, the ring C, Ar, and Q represent the same as those in the formula (101); k is 1 or 2; and rings D and E each are a substituted or unsubstituted five- to seven-membered ring including as a ring-forming atom an atom selected from a carbon atom, a nitrogen atom, an oxygen atom, a sulfur atom, and a silicon atom.

The compound represented by the formula (101) is preferably compounds represented by the following formulae.

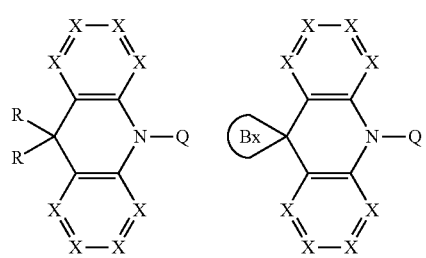

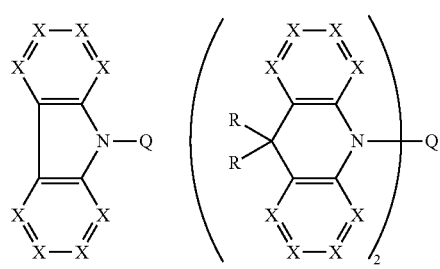

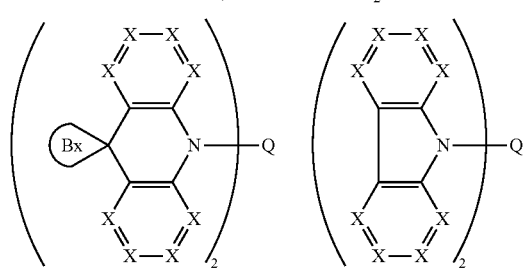

In the formulae: R represents an alkyl group; X represents CH, CRx or a nitrogen atom; Rx represents a substituent; and Bx represents a five- to seven-membered ring formed of carbon atoms.

The compound represented by the formula (101) is further preferably compounds represented by the following formulae.

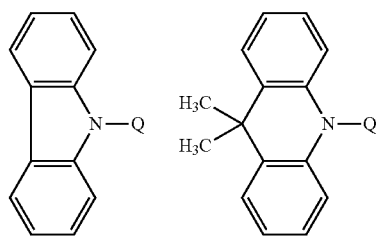

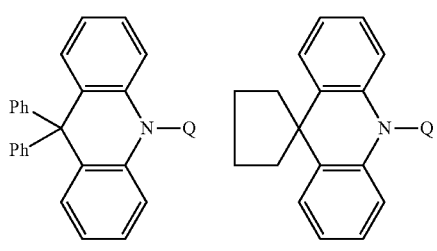

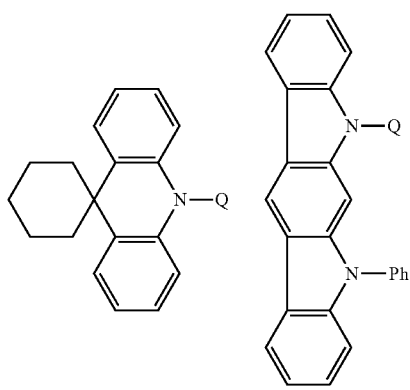
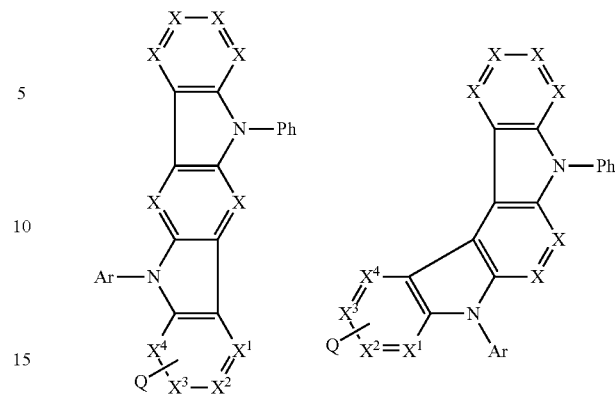
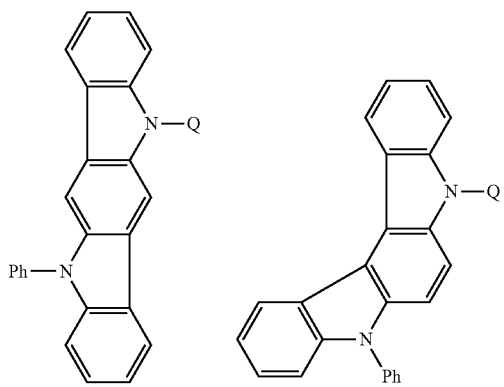

The compound represented by the formula (102) is preferably compounds represented by the following formulae.

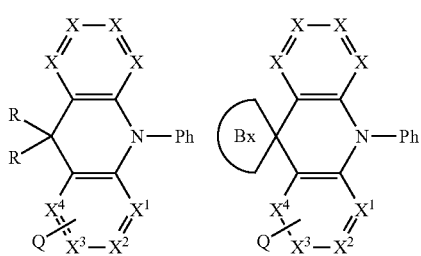
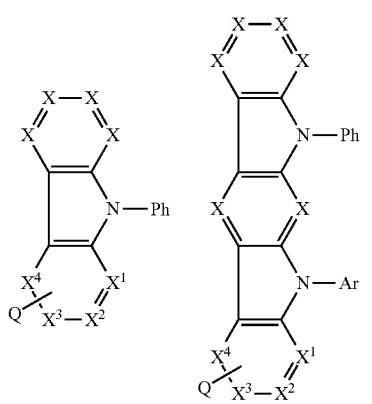

In the formulae: R represents an alkyl group; X and $X^1$ to $X^4$ represent CH, CRx or a nitrogen atom; Rx represents a substituent; one of $X^1$ to $X^4$ is a carbon atom bonded to Q; Bx represents a five- to seven-membered ring formed in a carbon atom; Ar represents an aromatic hydrocarbon group; and Ph represents a phenyl group.

Among the compounds represented by the formulae, $X^1$ or $X^3$ is preferably a carbon atom bonded to Q.

The compound represented by the formula (102) is further preferably compounds represented by the following formulae.

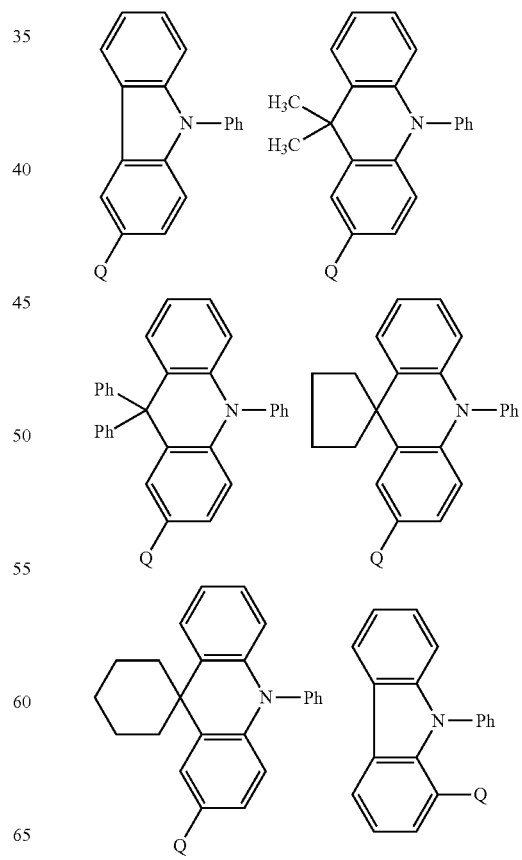

-continued
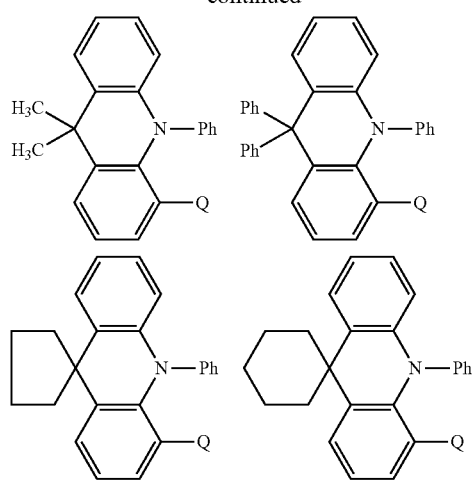
A group represented by the formula (103) is preferably groups represented by the following formulae.
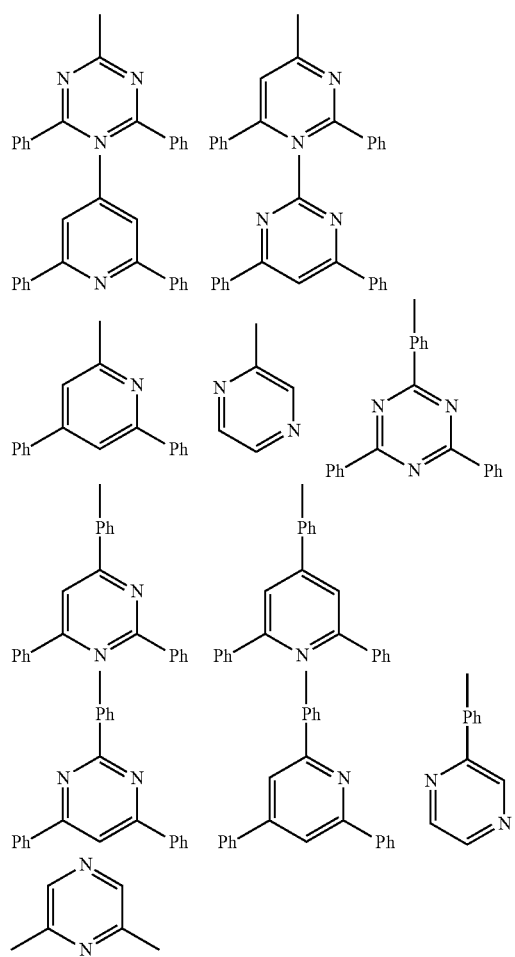
In the formulae: Ph represents a phenyl group.
Examples of the compound used as the host material in the exemplary embodiment are shown below. However, the host material in the exemplary embodiment is not limited thereto.
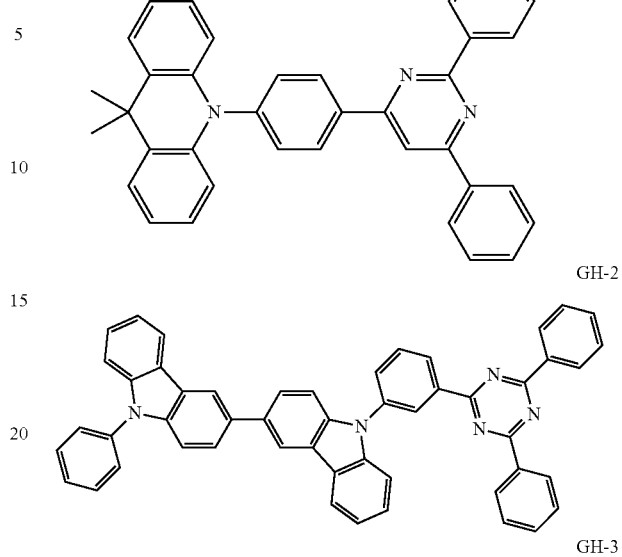
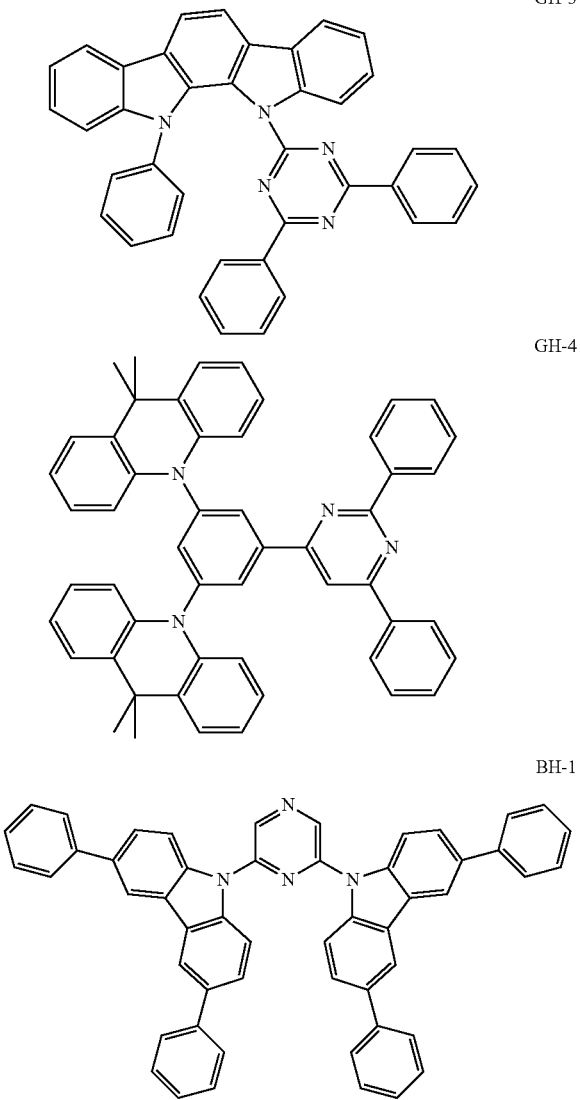

Dopant Material

In this exemplary embodiment, the fluorescent dopant material is used as the dopant material of the emitting layer as described above.

Known fluorescent materials are usable as the fluorescent dopant material. Examples of the fluorescent dopant material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative.

A thickness of the emitting layer is preferably in the range of 5 nm to 50 nm, more preferably in the range of 7 nm to 50 nm and most preferably in the range of 10 nm to 50 nm. The thickness of less than 5 nm may cause difficulty in forming the emitting layer and in controlling chromaticity, while the thickness of more than 50 nm may raise drive voltage.

In the emitting layer, a ratio of the host material and the fluorescent dopant material is preferably in a range of 99:1 to 50:50 at a mass ratio.

Substrate

The organic EL device according to the aspect of the invention is formed on a light-transmissive substrate. The light-transmissive substrate supports an anode, an organic compound layer, a cathode and the like of the organic EL device. The light-transmissive substrate is preferably a smoothly-shaped substrate that transmits 50% or more of light in a visible region of 400 nm to 700 nm.

The light-transmissive plate is exemplarily a glass plate, a polymer plate or the like.

The glass plate is formed of soda-lime glass, barium/strontium-containing glass, lead glass, aluminosilicate glass, borosilicate glass, barium borosilicate glass, quartz and the like.

The polymer plate is formed of polycarbonate, acryl, polyethylene terephthalate, polyether sulfide and polysulfone.

Anode and Cathode

The anode of the organic EL device injects holes into the emitting layer, so that it is efficient that the anode has a work function of 4.5 eV or higher.

Exemplary materials for the anode are indium-tin oxide (ITO), tin oxide (NESA), indium zinc oxide, gold, silver, platinum and copper.

When light from the emitting layer is to be emitted through the anode, the anode preferably transmits more than 10% of the light in the visible region. Sheet resistance of the anode is preferably several hundreds Ω/sq. or lower. The thickness of the anode is typically in the range of 10 nm to 1 μm, and preferably in the range of 10 nm to 200 nm, though it depends on the material of the anode.

The cathode is preferably formed of a material with smaller work function in order to inject electrons into the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode, the cathode may be made by forming a thin film on, for instance, the electron transporting layer and the electron injecting layer by a method such as vapor deposition.

In addition, the light from the emitting layer may be emitted through the cathode. When light from the emitting layer is to be emitted through the cathode, the cathode preferably transmits more than 10% of the light in the visible region.

Sheet resistance of the cathode is preferably several hundreds Ω/sq. or lower.

The thickness of the cathode is typically in the range of 10 nm to 1 μm, and preferably in the range of 50 nm to 200 nm, though it depends on the material of the cathode.

Hole Injecting/Transporting Layer

The hole injection/transport layer helps injection of holes to the emitting layer and transport the holes to an emitting region. A compound having a large hole mobility and a small ionization energy is used as the hole injection/transport layer.

A material for forming the hole injection/transport layer is preferably a material of transporting the holes to the emitting layer at a lower electric field intensity. For instance, an aromatic amine compound is preferably used.

Electron Injecting/Transporting Layer

The electron injecting/transporting layer helps injection of the electrons into the emitting layer and transports the electrons to an emitting region. A compound having a large electron mobility is used as the electron injecting/transporting layer.

A preferable example of the compound used as the electron injecting/transporting layer is an aromatic heterocyclic compound having at least one heteroatom in a molecule. Particularly, a nitrogen-containing cyclic derivative is preferable. The nitrogen-containing cyclic derivative is preferably a heterocyclic compound having a nitrogen-containing six-membered or five-membered ring skeleton.

In the organic EL device in the exemplary embodiment, in addition to the above exemplary compound, any compound selected from compounds known as being used in the typical organic El device is usable as a compound for the organic compound layer other than the emitting layer.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Thickness

The thickness of each organic layer of the organic EL device in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Modifications of Exemplary Embodiment

It should be noted that the invention is not limited to the above exemplary embodiment but may include any modification and improvement as long as such modification and improvement are compatible with the invention.

The emitting layer is not limited to a single layer, but may be provided as laminate by a plurality of emitting layers. When the organic EL device includes the plurality of emitting layers, it is only required that at least one of the emitting layers includes the host material and the fluorescent dopant material defined in the exemplary embodiment. The others of the emitting layers may be a fluorescent emitting layer or a phosphorescent emitting layer.

When the organic EL device includes the plurality of emitting layers, the plurality of emitting layers may be adjacent to each other.

Further, the materials and treatments for practicing the invention may be altered to other arrangements and treatments as long as such other arrangements and treatments are compatible with the invention.

EXAMPLES

Examples of the invention will be described below. However, the invention is not limited by these Examples.

Used compounds are as follows.

HI-1

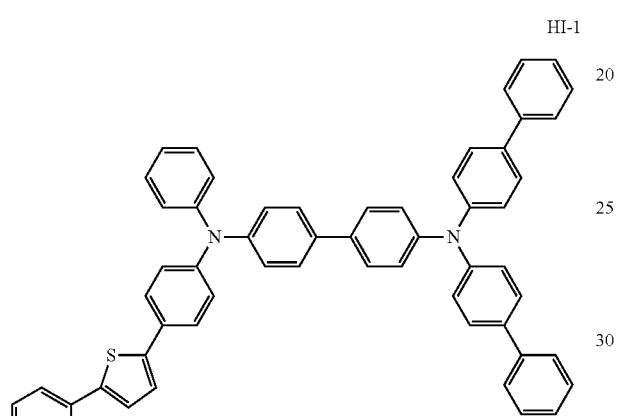

GD-1

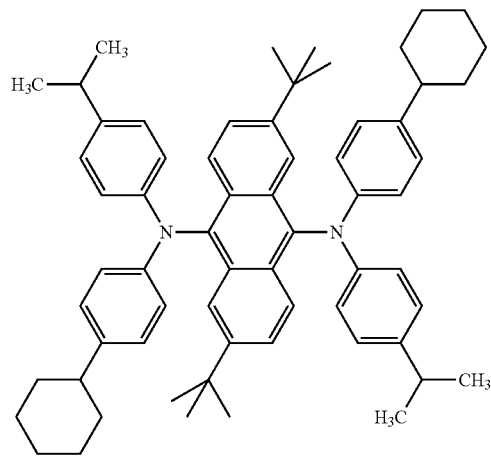

ET-1

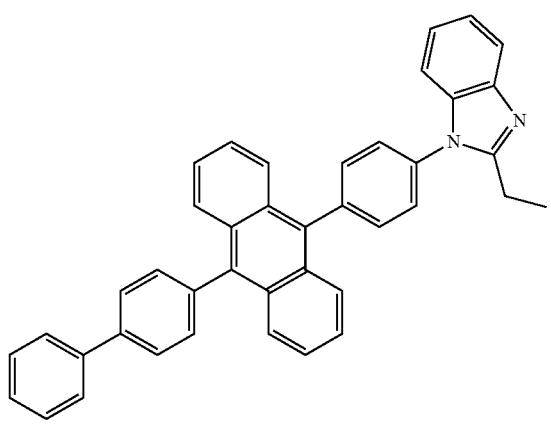

HI-2

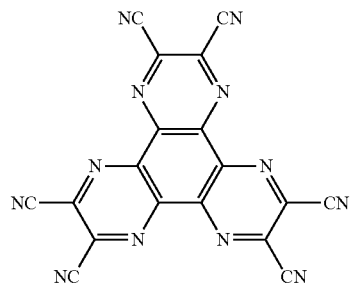

HT-1

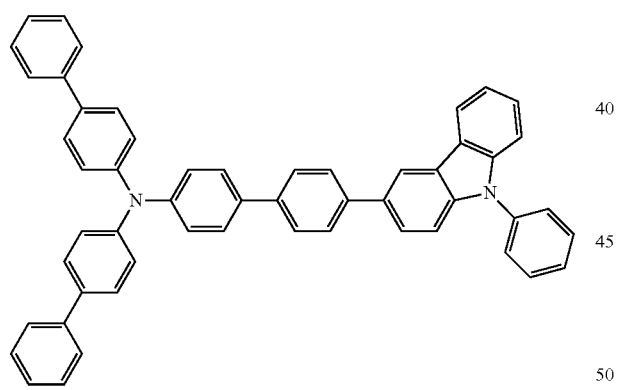

GH-4

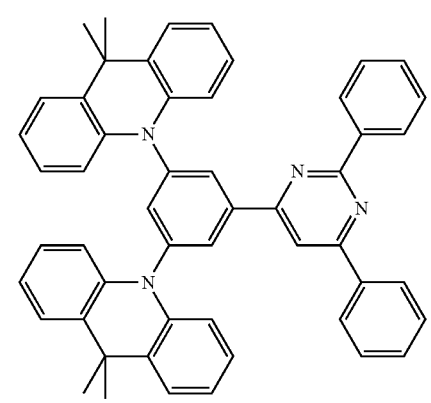

HT-2

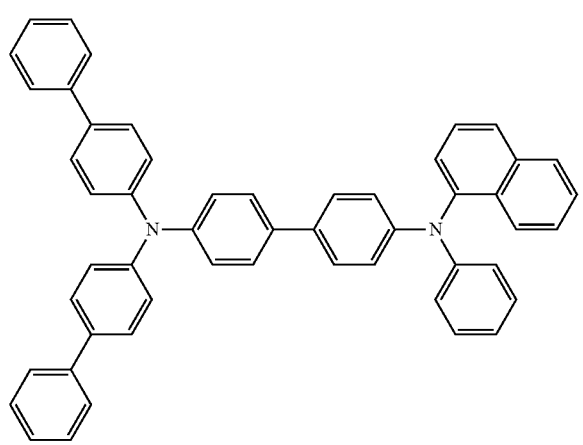

HT-3

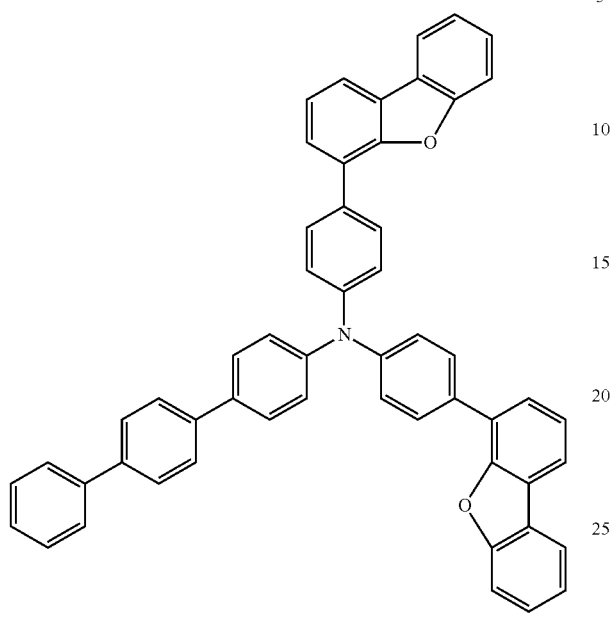

ET-2

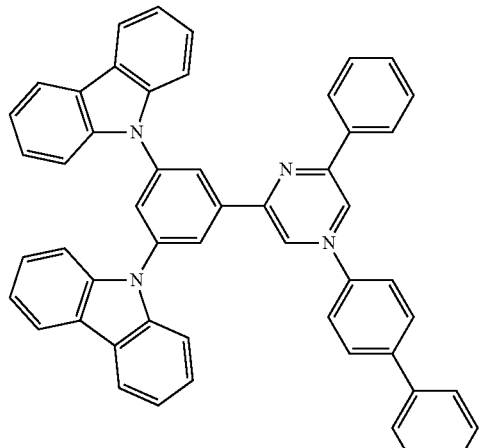

BH-1

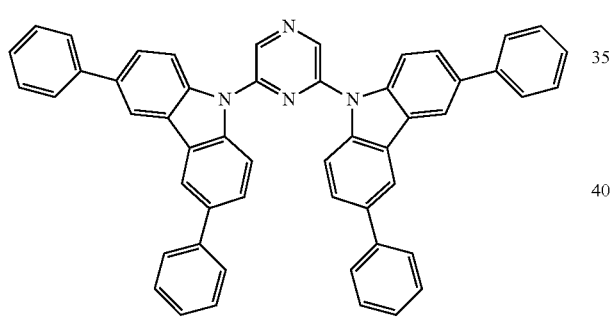

ET-3

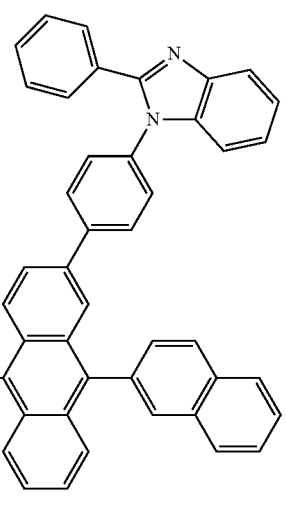

Liq

BD-1

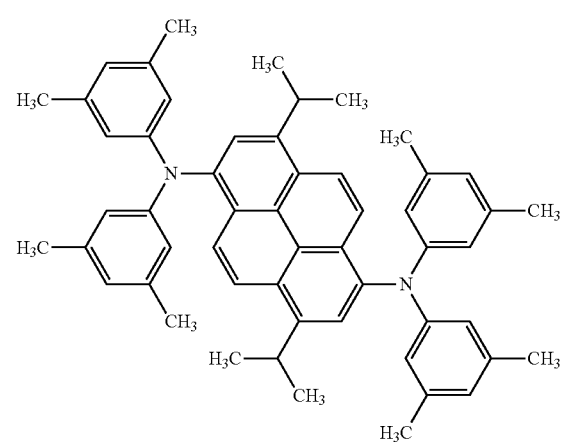

Synthesis of Compound(s)

Synthesis Example 1

Synthesis of GH-4

Under an argon gas atmosphere, an intermediate A (4.4 g, 21 mmol) synthesized according to the method described in JP-A-2010-180204, an intermediate B (4.7 g, 10 mmol) synthesized according to the method described in International Publication No. WO03/080760, tris(dibenzylidene acetone) dipalladium (0.37 g, 0.4 mmol), tri-t-butylphosphonium tetrafluoroborate (0.46 g, 1.6 mmol), t-butoxysodium (2.7 g, 28 mmol) and anhydrous toluene (100 ml) were sequentially added and refluxed for eight hours.

After the reaction solution was cooled down to the room temperature, an organic layer was separated and an organic solvent was distilled away under reduced pressure. The obtained residue was refined by silica-gel column chromatography, so that a target compound GH-4 (3.6 g, a yield of 50%) was obtained.

FD-MS analysis consequently showed that m/e was equal to 722 while a calculated molecular weight was 722.

A synthesis scheme of the target compound GH-4 is shown below.

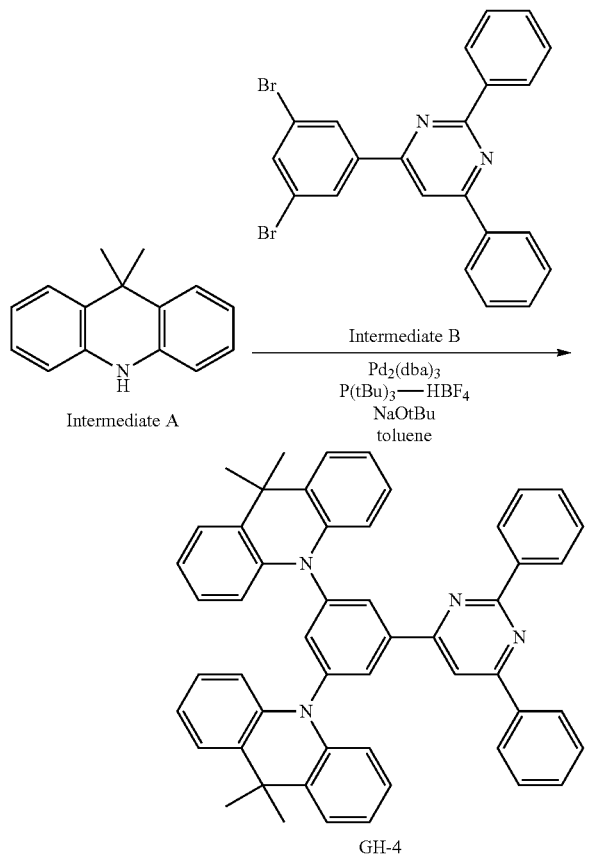

GH-4

Synthesis Example 2

Synthesis of BH-1

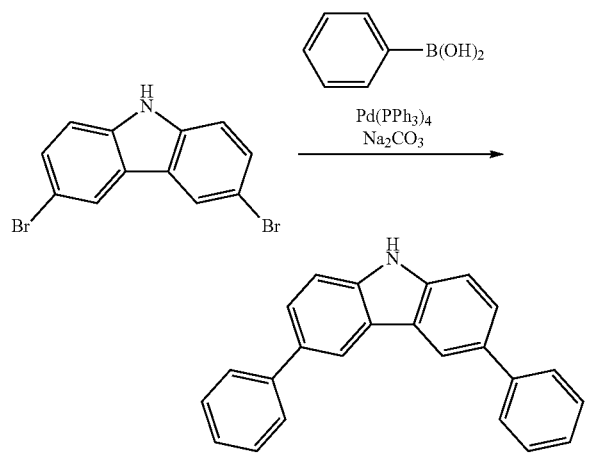

Under a nitrogen gas atmosphere, to a flask, 3,6-dibromocarbazole (5 g, 15.4 mmol), phenylboronic acid (4.1 g, 33.9 mmol), tetrakis(triphenylphosphine)palladium (0.7 g, 0.6 mmol), toluene (45 ml) and 2M sodium carbonate (45 ml) were mixed in sequence, and were stirred for eight hours at 80 degrees C. An organic phase was separated and then concentrated under reduced pressure by an evaporator. The obtained residue thereof was refined by silica-gel column chromatography, so that 3,6-diphenylcarbazole (3.6 g, a yield of 74%) was obtained.

Under an argon gas atmosphere, 2,6-dichloropyrazine (0.6 g, 3.9 mmol), 3,6-dibromocarbazole (2.6 g, 8 mmol), tris(dibenzylideneacetone)dipalladium (0.07 g, 0.08 mmol), tri-t-butylphosphonium tetrafluoroborate (0.09 g, 0.3 mmol), sodium t-butoxide (0.5 g, 5.5 mmol), and anhydrous toluene (20 ml) were mixed in sequence, and heated to reflux for 8 hours.

After the reaction solution was cooled down to the room temperature, an organic layer was removed and an organic solvent was distilled away under reduced pressure. The obtained residue thereof was refined by silica-gel column chromatography, so that 1.8 g of a solid was obtained.

FD-MS analysis consequently showed that the obtained compound was identified as a compound BH-1.

FD-MS: calcd for $C_{52}H_{34}N_4$=714. Found m/z=714 (M+, 100)

Evaluation of Compounds

Next, properties of the compounds used in Example were measured. The target compounds are GH-4, GD-1, BH-1, and BD-1. A measurement method or a calculation method is described below. Measurement results or calculation results are shown in Table 1.

(1) Singlet Energy EgS

Singlet Energy EgS was obtained according to the following method.

The target compound to be measured was evaporated on a quartz substrate to prepare a sample. An absorption spectrum of the sample was measured at a normal temperature (300K). A sample was 100 nm thick. The absorption spectrum was expressed in coordinates of which ordinate axis indicated absorbance and of which abscissa axis indicated the wavelength. A tangent was drawn to the fall of the absorption spectrum on the long-wavelength side, and a wavelength value λedge (nm) at an intersection of the tangent and the abscissa axis was obtained. The wavelength value was converted to an energy value by the following conversion equation. The energy value was defined as EgS.

The conversion equation: $EgS$ (eV)=1239.85/λedge

For the measurement of the absorption spectrum, a spectrophotometer (U3310 manufactured by Hitachi, Ltd.) was used.

The tangent to the fall of the absorption spectrum on the long-wavelength side was drawn as follows. While moving on a curve of the absorption spectrum from the maximum spectral value closest to the long-wavelength side in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength side (except when absorbance is 0.1 or less) is defined as the tangent to the fall of the absorption spectrum on the long-wavelength side.

The maximum absorbance of 0.2 or less was not included in the above-mentioned maximum absorbance on the long-wavelength side.

(2) Energy Gap $Eg_{77K}$ and Triplet Energy $EgT_D$ $Eg_{77K}$ and $EgT_D$ were obtained by the following method.

Each of the compounds was measured by a known method of measuring phosphorescence (e.g. a method described in "Hikarikagaku no Sekai (The World of Photochemistry)" (edited by The Chemical Society of Japan, 1993, on and near page 50). Specifically, each compound was dissolved in a solvent (EPA (diethylether:isopentane:ethanol=5:5:5 (volume ratio), a spectral grade solvent) to provide a sample for phosphorescence measurement (Sample 10 μmol/liter). The sample for phosphorescence measurement was put into a quartz cell, cooled to 77K and irradiated with excitation light, so that phosphorescence intensity was measured while changing a wavelength. The phosphorescence spectrum was expressed in coordinates of which ordinate axis indicated phosphorescence intensity and of which abscissa axis indicated the wavelength.

A tangent was drawn to the rise of the phosphorescent spectrum on the short-wavelength side, and a wavelength value λedge (nm) at an intersection of the tangent and the abscissa axis was obtained. The wavelength value was converted to an energy value by the following conversion equation. The energy value was defined as $Eg_{77K}(H)$ or $EgT_D$ ($Eg_{77K}(D)$).

The conversion equation: $Eg_{77k}(H)$ (eV)=1239.85/λedge

:$EgT_D$ (eV)=1239.85/λedge

The tangent to the rise of the phosphorescence spectrum on the short-wavelength side was drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination was defined as the tangent to the rise of the phosphorescence spectrum on the short-wavelength side.

The maximum with peak intensity being 10% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 and optional accessories for low temperature measurement (which were manufactured by Hitach High-Technologies Corporation) were used. The measurement instrument is not limited to this arrangement. A combination of a cooling unit, a low temperature container, an excitation light source and a light-receiving unit may be used for measurement.

(3) ΔST

ΔST was obtained as a difference between EgS and $Eg_{77K}$ measured in the above (1) and (2) (see the above formula (2)). The results are shown in Table 1.

(4) ΔT

ΔT was obtained as a difference between $Eg_{77K}(H)$ and EgT(D) measured in the above (1) and (2).

$\Delta T = Eg_{77K}(H) - EgT(D)$

In a combination of the host material GH-4 and the dopant material GD-1, the following formula was satisfied.

$\Delta T = 1.11$ (eV)

It should be noted that ΔT was not obtained because EgT (D) of the dopant material BD-1 was not measured in a combination of the host material BH-1 and the dopant material BD-1.

The dopant material GD-1 was measured in a range of $10^{-5}$ to $10^{-6}$ mol/l of a concentration in a toluene solution using Absolute PL Quantum Yield Measurement System C9920-02 manufactured by HAMAMATSU PHOTONICS K.K. As a result, an absolute PL quantum yield was 100%.

The dopant material BD-1 was measured in a range of $10^{-5}$ to $10^{-6}$ mol/l of a concentration in a toluene solution using Absolute PL Quantum Yield Measurement System C9920-02 manufactured by HAMAMATSU PHOTONICS K.K. As a result, an absolute PL quantum yield was 90%.

A compound HT-1 in a form of a thin film was measured in terms of ionization potential (also referred to as IP) using a photoelectron spectroscopy (AC-3: manufactured by RIKEN KEIKI Co., Ltd.). As a result, IP was 5.6 eV.

A half bandwidth of photoluminescence spectrum was obtained as follows.

Each compound was dissolved in a solvent (dichloromethane) to prepare a sample for fluorescence measurement (Sample 10 μmol/liter). The sample for fluorescence measurement was put into a quartz cell and irradiated with excitation light at a normal temperature (300K), so that fluorescence intensity was measured while changing a wavelength. The photoluminescence spectrum was expressed in coordinates of which ordinate axis indicated fluorescence intensity and of which abscissa axis indicated the wavelength. For fluorescence measurement, a spectrophotofluorometer F-4500 (manufactured by Hitach High-Technologies Corporation) was used.

The half bandwidth (unit: nm) was measured based on the photoluminescence spectrum.

The compounds GH-4 and BH-1 were measured with respect to the half bandwidth. As a result, the half bandwidth of the compounds GH-4 and BH-1 were respectively 79 nm and 98 nm.

TABLE 1

|  | EgS [eV] | Eg77K [eV] | Δ ST [eV] |
|---|---|---|---|
| GH-4 | 2.98 | 2.91 | 0.07 |
| GD-1 | 2.47 | 1.80 | 0.67 |
| BH-1 | 2.90 | 2.84 | 0.06 |
| BD-1 | 2.69 | — | — |

Preparation and Evaluation of Organic EL Device

The organic EL device was prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, the compound HI-1 was evaporated on a surface of the glass substrate where the transparent electrode line was provided in a manner to cover the transparent electrode, thereby forming a 50-nm thick film of the compound HI-1. The HI-1 film serves as a hole injecting layer.

After the film formation of the HI-1 film, a compound HT-1 was evaporated on the HI-1 film to form a 60-nm thick HT-1 film. The HT-1 film serves as a hole transporting layer.

The compound GH-4 (the host material) and the compound GD-1 (the fluorescent dopant material) were co-evaporated on the HT-1 film to form a 30-nm thick emitting layer. The concentration of the dopant material was set at 5 mass %.

An electron transporting compound ET-1 was evaporated on the emitting layer to form a 25-nm thick electron transporting layer.

LiF was evaporated on the electron transporting layer to form a 1-nm thick LiF film.

A metal Al was evaporated on the LiF film to form an 80-nm thick metal cathode.

Thus, the organic EL device of Example 1 was prepared.

A device arrangement of the organic EL device in Example 1 is schematically shown as follows.

ITO(130)/HI-1(50)/HT-1(60)/GH-4:GD-1(30.5%)/ET-1(25)/LiF(1)/Al(80)

Numerals in parentheses represent a film thickness (unit: nm). Numerals represented by percentage in the same parentheses represent a ratio (mass %) of an added component such as the fluorescent dopant material in the emitting layer.

Evaluation of Organic EL Devices

The prepared organic EL devices were evaluated in terms of drive voltage, CIE1931 chromaticity, current efficiency L/J, power efficiency, external quantum efficiency EQE, and delayed fluorescence ratio. The evaluation items other than the delayed fluorescence ratio were measured under the current density of 1.00 mA/cm$^2$ and 10.00 mA/cm$^2$. Evaluations of the results under the current density of 1.00 mA/cm$^2$ and 10.00 mA/cm$^2$ are respectively shown as Evaluation Example 1 and Evaluation Example 2. The results are shown in Table 2.

Drive Voltage

Voltage was applied between ITO and Al such that the current density was 1.00 mA/cm$^2$ or 10.00 mA/cm$^2$, where the voltage (unit: V) was measured.

CIE1931 Chromaticity

Voltage was applied on each of the organic EL devices such that the current density was 1.00 mA/cm$^2$ or 10.00 mA/cm$^2$, where CIE1931 chromaticity coordinates (x, y) were measured using a spectroradiometer CS-1000 (manufactured by Konica Minolta Holdings, Inc.).

Current Efficiency L/J and Power Efficiency η

Voltage was applied on each of the organic EL devices such that the current density was 1.00 mA/cm$^2$ or 10.00 mA/cm$^2$, where spectral radiance spectra were measured by the aforementioned spectroradiometer. Based on the obtained spectral radiance spectra, the current efficiency (unit: cd/A) and the power efficiency ç (unit: lm/W) were calculated.

Main Peak Wavelength $\lambda_p$

A main peak wavelength $\lambda_p$ was calculated based on the obtained spectral-radiance spectra.

External Quantum Efficiency EQE

The external quantum efficiency EQE (unit: %) was calculated based on the obtained spectral-radiance spectra, assuming that the spectra was provided under a Lambertian radiation.

TABLE 2

|  | Current Density (mA/cm$^2$) | Voltage (V) | Luminous Intensity (nit) | L/J (cd/A) | η (lm/W) | CIE-x | CIE-y | λ (nm) | EQE (%) |
|---|---|---|---|---|---|---|---|---|---|
| Evaluation Example 1 | 10.00 | 3.97 | 1585.2 | 15.85 | 12.85 | 0.274 | 0.606 | 520 | 4.59 |
| Evaluation Example 2 | 1.00 | 3.44 | 174.0 | 17.40 | 15.89 | 0.276 | 0.604 | 522 | 5.04 |

As shown in Table 2, even when the current density was increased from 1.00 mA/cm$^2$ to 10.00 mA/cm$^2$, the external quantum efficiency was not largely reduced. Accordingly, it was recognized that the organic EL device of Example 1 emits light with a high efficiency even in the high current density area.

Delayed Fluorescence Ratio

Voltage pulse waveform (pulse width: 500 micro second, frequency: 20 Hz, voltage: equivalent to 0.1 to 100 mA/cm$^2$) output from a pulse generator 8114A (manufactured by Agilent Technologies) was applied. EL emission was input in a photomultiplier R928 (manufactured by HAMAMATSU PHOTONICS K.K.). The pulse voltage waveform and the EL emission were synchronized and loaded in an oscilloscope 2440 (manufactured by Tektronix) to obtain a transitional EL waveform. A value before the elapse of 10$^{-5}$ seconds of the transitional EL waveform calculated by the method of least squares was fitted in a linear line to determine a delayed fluorescence ratio.

Voltage of 0.14 mA/cm$^2$ was applied on the organic EL device of the Example 1 at the room temperature, where the transitional EL waveform is shown in FIG. 6A. The pulse voltage was removed at the time of about 3×10$^{-8}$ seconds.

In the graph of FIG. 6B, the voltage removal time is a starting point and the inverse square root of luminous intensity before the elapse of $1.5 \times 10^{-5}$ seconds after voltage removal is plotted in an approximately linear line. The delayed fluorescence ratio of the organic EL device in Example 1 was 41% according to the graph. This delayed fluorescence ratio exceeds the theoretical upper-limit (37.5%) of the TTF ratio.

It was read from the graph in FIG. 6A that a residual intensity ratio in 1 μs was 39.8%.

Relationship Between Current Efficiency and Current Density

Figure 9:
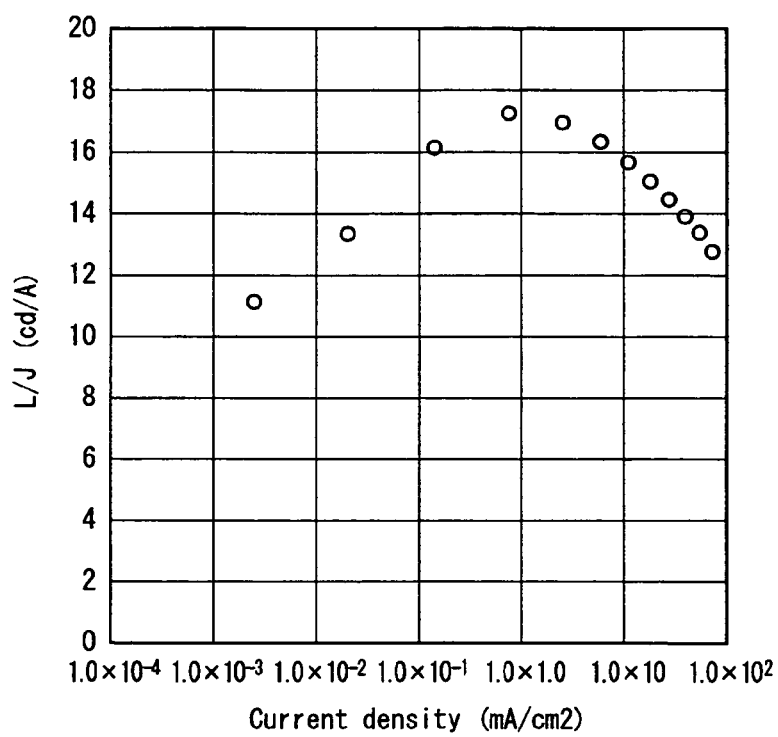
FIG. 9 is a graph showing a relationship between a current efficiency and a current density.

The organic EL device of Example 1 was measured in terms of the current efficiency in accordance with changes of the current density. FIG. 9 shows measurement results as a graph showing a relationship of the current efficiency.

As shown in FIG. 9, the current efficiency was higher in the current density area of 1 mA/cm² to 10 mA/cm² than at the current density of 0.01 mA/cm².

Example 2

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 70 nm thick.

After the glass substrate having the transparent electrode line was cleaned, the glass substrate was mounted on a substrate holder of a vacuum evaporation apparatus. Initially, the compound HI-2 was evaporated on a surface of the glass substrate where the transparent electrode line was provided in a manner to cover the transparent electrode, thereby forming a 5-nm thick film of the compound HI-2. The HI-2 film serves as a hole injecting layer.

After the film formation of the HI-2 film, a compound HT-2 was evaporated on the HI-2 film to form a 125-nm thick HT-2 film. After the film formation of the HT-2 film, the compound HT-3 was deposited on the HT-2 film to form a 25-nm thick HT-3 film. The HT-2 film and the HT-3 film serve as a hole transporting layer.

A compound BH-1 (a host material) and a compound BD-1 (a fluorescent dopant material) were co-evaporated on the HT-3 film to form a 25-nm thick emitting layer. The concentration of the dopant material was set at 4 mass %.

An electron transporting compound ET-2 was evaporated on the emitting layer to form a 5-nm thick hole blocking layer.

ET-3 and Liq were co-evaporated on the hole blocking layer to form a 20-nm thick electron transporting layer. A concentration ratio between ET-3 and Liq was set at 50 mass %:50 mass %.

Liq was evaporated on the electron transporting layer to form a 1-nm thick Liq film.

A metal Al was evaporated on the Liq film to form an 80-nm thick metal cathode.

Thus, the organic EL device of Example 2 was prepared.

A device arrangement of the organic EL device in Example 2 is schematically shown as follows.

ITO(70)/HI-2(5)/HT-2(125)/HT-3(25)/BH-1:BD-1(25.4%)/ET-2(5)/ET-3Liq(20,50%)/Liq(1)/Al(80)

Numerals in parentheses represent a film thickness (unit: nm). The numerals represented by percentage in parentheses indicate a ratio (mass percentage) of BD-1 and Liq.

Evaluation of Organic EL Devices

The prepared organic EL devices were evaluated in terms of drive voltage, CIE1931 chromaticity, current efficiency L/J, power efficiency, external quantum efficiency EQE, and delayed fluorescence ratio. Evaluation items other than the delayed fluorescence ratio were evaluated as Evaluation Example 3 in the same manner as in Example at 1.00 mA/cm² of the current density. The results are shown in Table 3.

TABLE 3

| | Current Density (mA/cm²) | Voltage (V) | Luminous Intensity (nit) | L/J (cd/A) | η (lm/W) | CIE-x | CIE-y | λ (nm) | EQE (%) |
|---|---|---|---|---|---|---|---|---|---|
| Evaluation Example 3 | 1.00 | 3.81 | 57.62 | 5.76 | 4.75 | 0.13 | 0.197 | 471 | 4.16 |

Delayed Fluorescence Ratio

A transitional EL waveform was obtained in the same manner as in Example 1. A value before the elapse of $10^{-5}$ seconds of the transitional EL waveform calculated by the method of least squares was fitted in a linear line and was analyzed to determine a delayed fluorescence ratio.

Figure 10:
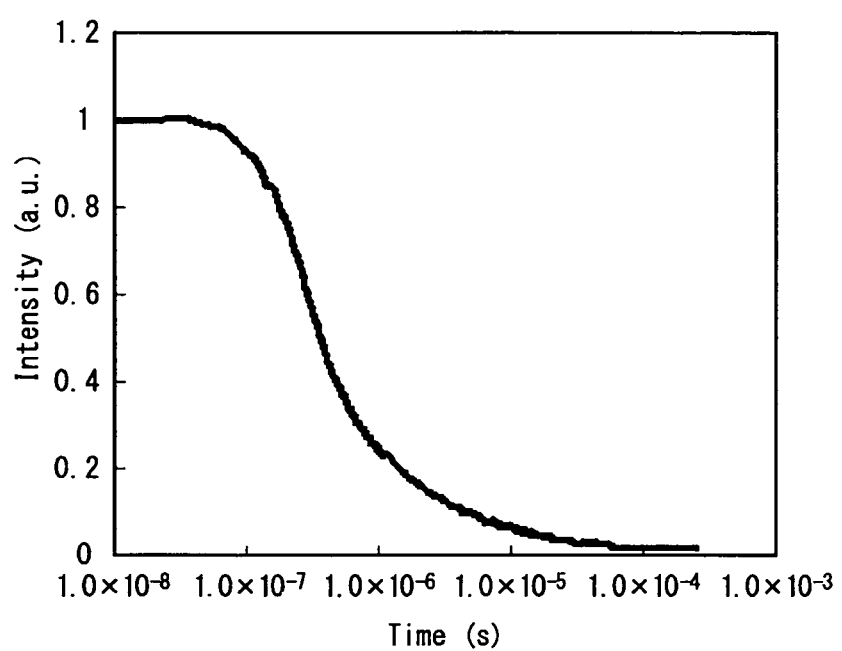
FIG. 10 is a graph showing time-varying luminous intensities of the EL device.

Voltage of 1.00 mA/cm² was applied on the organic EL device of the Example 2 at the room temperature, where the transitional EL waveform is shown in FIG. 10. The pulse voltage was removed at the time of about $3 \times 10^{-8}$ seconds.

Based on the graph, where the voltage removal time was a starting point and the inverse square root of luminous intensity before the elapse of $1.0 \times 10^{-5}$ seconds after voltage removal were plotted in the same manner as in Example 1, a delayed fluorescence ratio was obtained. The delayed fluorescence ratio of the organic EL device in Example 2 was 38.7%. This delayed fluorescence ratio exceeds the theoretical upper-limit (37.5%) of the TTF ratio.

Residual Intensity Ratio in 1 μs

It was read from the graph in FIG. 10 that a residual intensity ratio in 1 μs was 36.3%.

Reference Example

Herein, the organic EL device described in Document 2 are shown as a reference example and compared with the organic EL device of Example 1 in terms of the device arrangement.

A device arrangement of the organic EL devices in the reference example is schematically shown below in the same manner as in Example 1. ITO(110)/NPD(40)/m-CP(10)/m-CP:PIC-TRZ(20.6%)/BP4mPy(40)/LiF(0.8)/Al(70)

Compounds used in the reference example will be shown below.

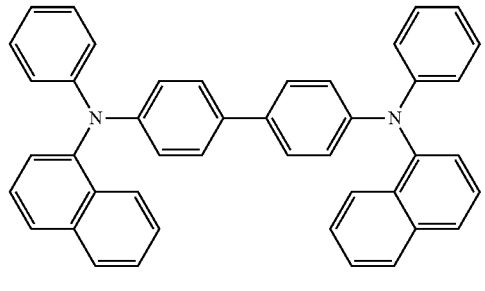

α-NPD

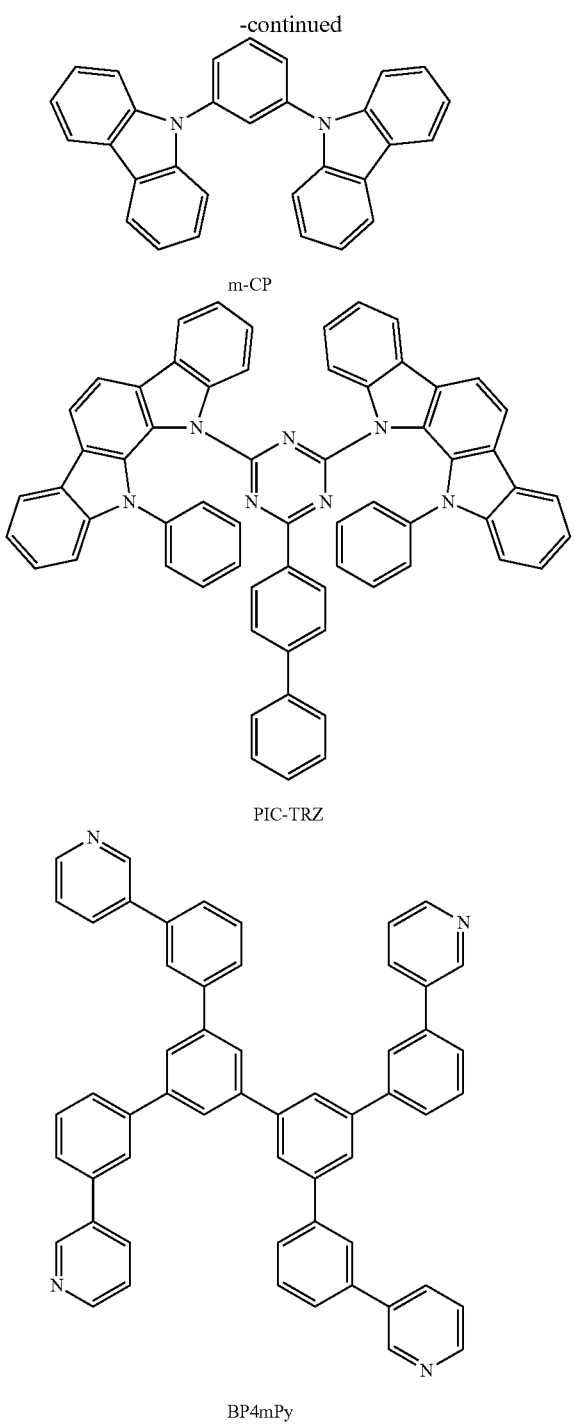

The device only exhibits the maximum EQE of 5.1% in the current density area of 0.01 mA/cm² which is much lower than the current density area in a practical use. Accordingly, in a high current density area around 1 to 10 mA/cm², roll-off is generated and a luminous efficiency is reduced.

Accordingly, it is recognized that the organic EL device of Example 1 emitted light with a high efficiency even in the high current density area.

What is claimed is:

1. An organic electroluminescence device comprising a pair of electrodes and an organic compound layer between the pair of electrodes, the organic compound layer comprising an emitting layer comprising a first material and a second material, wherein
the second material is a fluorescent material,
singlet energy EgS(H) of the first material and singlet energy EgS(D) of the second material satisfy a relationship of a formula (1) below, and
the first material satisfies a relationship of a formula (2) below in terms of a difference ΔST(H) between the singlet energy EgS(H) and an energy gap $Eg_{77K}$(H) at 77K $$EgS(H) > EgS(D) \tag{1}$$

$$\Delta ST(H) = EgS(H) - Eg_{77K}(H) < 0.3 \text{ (eV)}. \tag{2}$$

2. The organic electroluminescence device according to claim 1,
wherein the organic electroluminescence device exhibits a ratio of the luminous intensity due to delayed fluorescence relative to the total luminous intensity larger than 37.5%.

3. The organic electroluminescence device according to claim 1,
wherein the organic electroluminescence device exhibits a residual intensity ratio larger than 36.0% after the elapse of 1 μs after voltage removal in a transitional EL measurement, wherein the residual intensity ratio is a ratio of the luminous intensity due to delayed fluorescence relative to the total luminous intensity after the elapse of 1 μs.

4. The organic electroluminescence device according to claim 1, wherein a half bandwidth of a photoluminescence spectrum of the first material is 50 nm or more.

5. The organic electroluminescence device according to claim 1, wherein a half bandwidth of a photoluminescence spectrum of the first material is 75 nm or more.

6. The organic electroluminescence device according to claim 1, wherein
a difference ΔT between the energy gap $Eg_{77K}$(H) at 77K of the first material and an energy gap $Eg_{77K}$(D) at 77K of the second material satisfies a relationship of a formula (3) below $$\Delta T = Eg_{77K}(H) - Eg_{77K}(D) \geq 0.6 \text{ (eV)}. \tag{3}$$

* * * * *